(12) United States Patent
Bohon et al.

(10) Patent No.: US 8,810,264 B2
(45) Date of Patent: Aug. 19, 2014

(54) METHODS AND DEVICES FOR SENSING CORROSION UNDER INSULATION (CUI)

(75) Inventors: William Mark Bohon, McKinney, TX (US); Allan John Perkins, La Habra, CA (US)

(73) Assignee: BP Corporation North America Inc., Houston, TX (US)

( * ) Notice: Subject to any disclaimer, the term of this patent is extended or adjusted under 35 U.S.C. 154(b) by 396 days.

(21) Appl. No.: 13/224,553

(22) Filed: Sep. 2, 2011

(65) Prior Publication Data

US 2012/0056634 A1     Mar. 8, 2012

Related U.S. Application Data

(60) Provisional application No. 61/379,769, filed on Sep. 3, 2010.

(51) Int. Cl.
*G01N 17/00* (2006.01)

(52) U.S. Cl.
CPC .............. *G01N 17/00* (2013.01); *G01N 17/006* (2013.01)
USPC ....................................................... 324/700

(58) Field of Classification Search
CPC .............................. G01N 17/00; G01N 17/006
USPC ....................................................... 324/700
See application file for complete search history.

(56) References Cited

U.S. PATENT DOCUMENTS

| 5,036,287 | A | | 7/1991 | Serwatzky | |
|---|---|---|---|---|---|
| 5,132,620 | A | * | 7/1992 | Rempt | 324/244.1 |
| 5,243,298 | A | * | 9/1993 | Runner | 324/700 |
| 6,946,855 | B1 | * | 9/2005 | Hemblade | 324/700 |
| 7,719,292 | B2 | * | 5/2010 | Eden | 324/700 |
| 2002/0083993 | A1 | * | 7/2002 | Bohon et al. | 138/149 |
| 2007/0176773 | A1 | * | 8/2007 | Smolander et al. | 340/539.26 |
| 2009/0058427 | A1 | | 3/2009 | Materer et al. | |
| 2009/0195260 | A1 | | 8/2009 | Bell et al. | |

FOREIGN PATENT DOCUMENTS

EP     0060552 A2     9/1982

OTHER PUBLICATIONS

PCT International Search report and Written Opinion of the International Searching Authority mailed Mar. 21, 2012, in related International Application No. PCT/US2011/050296, 24 pages.

(Continued)

*Primary Examiner* — Jeff Natalini
(74) *Attorney, Agent, or Firm* — John L. Wood

(57) ABSTRACT

A method of sensing corrosion of a pipe covered by a layer of insulation comprises positioning a CUI sensor radially adjacent an outer surface of the pipe. The CUI sensor comprises a non-conductive base having a first end and a second end opposite the first end. In addition, the CUI sensor comprises a first test circuit mounted to the base. The first test circuit includes a first conductor, a second conductor, and a first testing element extending between the first conductor and the second conductor. Further, the method comprises exposing the first testing element to the same environment as the outer surface of the pipe. Still further, the method comprises determining whether the first testing element has corroded through. Moreover, the method comprises assessing whether corrosion of the pipe has occurred based on the determination of whether the first testing element has corroded through.

15 Claims, 39 Drawing Sheets

(56) References Cited

OTHER PUBLICATIONS

Seon Yeob Li et al., "Application of Steel Thin Film Electrical Resistance Sensor for in Situ Corrosion Monitoring", ScienceDirect, WWW.sciencedirect.com, Sensors and Acuators, Jan. 7, 2006, pp. 368-377, vol. B 120, No. 2, XP005812339, Elsevier S.A., Switzerland.

English Abstract from especenet.com, mailed Sep. 22, 1982, in application with Publication No. EP0060552, 2 pages.

* cited by examiner

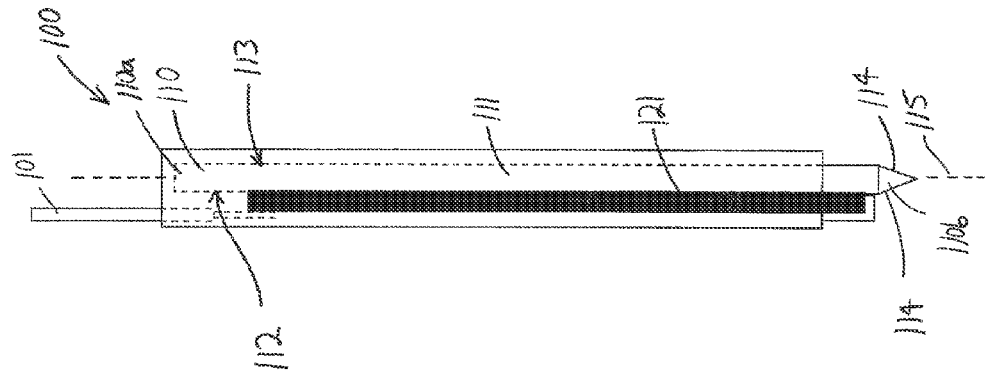
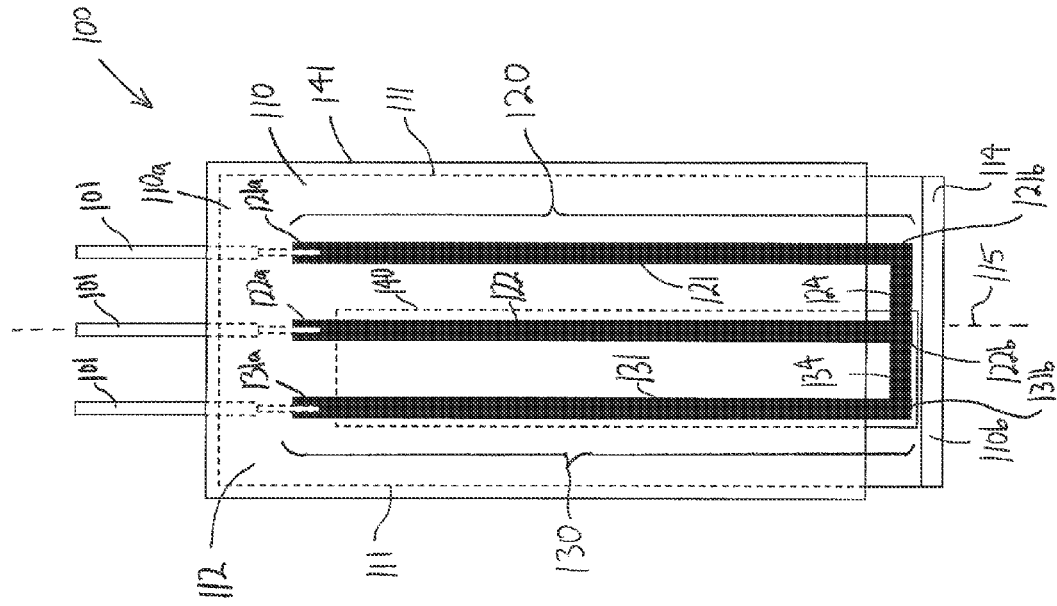

METHODS AND DEVICES FOR SENSING CORROSION UNDER INSULATION (CUI)

CROSS-REFERENCE TO RELATED APPLICATIONS

This application claims benefit of U.S. provisional patent application Ser. No. 61/379,769 filed Sep. 3, 2010, and entitled "Method and Apparatus for Sensing Corrosion Under Insulation (CUI)," which is hereby incorporated herein by reference in its entirety.

STATEMENT REGARDING FEDERALLY SPONSORED RESEARCH OR DEVELOPMENT

Not applicable.

BACKGROUND

1. Field of the Invention

This invention relates generally to the field of corrosion sensing. More specifically, the invention relates to methods and devices for sensing corrosion under insulation.

2. Background of the Technology

Corrosion Under Insulation (CUI) is a form of localized corrosion that has plagued insulated steel pipelines in the chemical and oil/gas industries for years. CUI-susceptible locations are often the result of legacy pipeline construction techniques. In particular, above-ground pipelines may be insulated with shop-applied, foam-in-place polyurethane foam insulation, usually 2 in. or 3 in. thick depending upon the pipe diameter. The foam insulation is protected by a galvanized steel jacketing, known as "spiral wrap" due to the distinctive corrugation pattern. When the insulation is applied to the joints of bare carbon steel pipe at the insulation shop, a couple of feet at either end of each joint are left uninsulated to facilitate pipeline construction in the field. After the pipe joints are welded together in the field, the gaps in insulation at each weld are subsequently insulated. This is done by bridging the insulation gap with 24-gage galvanized sheet steel, and then injecting foam-in-place polyurethane foam into the annulus between the pipe and the sheet steel jacketing. These field-applied sections of insulation are referred to as "weld packs."

For example, FIG. 1 illustrates a conventionally insulated pipeline 10 including a plurality of weld packs 20, and FIG. 2 illustrates one weld pack 20. Pipeline 10 includes a plurality of steel pipe segments 11 connected end-to-end with a welded joint 12. Pipe segments 11 are insulated with shop-applied foam insulation 13, which is protected with a galvanized steel spiral-wrap jacket 14. Shop-applied insulation 13 is not applied to the ends of pipe segments 11 so that adjacent segments 11 can be connected together in the field. Once segments 11 are connected together at joint 12, weld pack 20 is applied to insulate the ends of segments 11 and joint 11. In particular, the gap between the end faces of shop-applied insulation 13 is covered with a field-applied steel jacket 15, foam insulation 16 is injected in the annulus between jacket 15 and pipe segments 11, and a pair of annular seals 17 are disposed between jacket 15 and jackets 14 to prevent moisture from reaching insulation 16 and segments 11.

Due to thermal expansion, wind-induced vibration, aging, and other factors, the weather seals 17 between the shop-applied spiral wrap jacket 14 and the field-applied jacket 15 are particularly susceptible to failure. This provides opportunity for rain, dew, melting snow, or other moisture to pass between jackets 14, 15 and into insulation 16.

The polyurethane foam insulation 16 is typically closed cell foam and does not take up water readily. Although the mechanism is not fully understood, over long periods of time, moisture enters insulation 16 and slowly migrates through towards the carbon steel pipe segments 11 therewithin. This process may take up to several years. While this is happening, oxygen (air) is also diffusing through insulation 16 along with the water. Although the closed-cell polyurethane foam insulation 16 is not permeable to liquid water, it is somewhat permeable to gases such as water vapor and oxygen.

Once liquid water and oxygen reaches the surface of the carbon steel pipe segments 11, corrosion may initiate. The rate of corrosion depends upon many things such as the degree of wetness, the availability of oxygen, and the temperature of pipe segments 11. CUI is most aggressive on hot pipes, and many pipelines operate at about 140° F. At this elevated temperature, CUI can occur at rates of up to 40 mpy (mils per year) or more.

CUI does not occur until liquid water reaches the surface of a carbon steel pipe segment 11. Accordingly, one conventional approach for monitoring CUI is to use simple moisture sensors. However, this approach has several drawbacks. First, the moisture sensor must be particularly positioned because the radially outer portions of insulation 16 become wet long before (many years) the radially inner portion of insulation 16 adjacent the pipe segment 11. Thus, to be useful, the moisture sensor must only detect moisture in the insulation very near the surface of the pipe segment 11. Further, moisture sensors may be problematic as CUI indicators since they typically only indicate the immediate presence of moisture and not the past presence of moisture. More specifically, some weld packs (e.g., weld packs 20) go through periodic wet/dry cycles. For example, liquid water may periodically (e.g., annually) reach the pipe, initiate corrosion, and dry out. Consequently, a moisture sensor that only indicates the current presence of moisture may give misleading signals if insulation 16 has dried out at the particular time the sensor is being read. In other words, a simple moisture sensor may not indicate that this has occurred if it only detects the current presence of moisture and a reading was taken at a time when insulation 16 happened to be dry.

Even if moisture has reached a pipe segment 11, it is not necessarily an indication that corrosion is occurring (at a significant rate). There are numerous locations where, per a tangential radiographic testing (TRT) inspection, water has apparently reached the surface of a pipe segment, but detectable corrosion has not occurred. This often happens on pipelines that are cool (e.g., ~60 F) as the temperature is not sufficient to drive the corrosion reaction at a rate to generate significant (detectable) corrosion. Consequently, simple moisture sensors on these pipelines would be of little value.

Another conventional technique to monitor and detect CUI is periodic tangential radiographic testing (TRT) inspections. For TRT inspections, a crew starts at one end of a pipeline that is due for CUI inspection. The crew assembles a TRT trolley on the top of a pipeline and then moves the trolley along the pipeline until they encounter a weld pack. The crew inspects the weld pack for CUI with the TRT trolley and immediately records the results in a database. The vast majority of the time, no corrosion is detected at the weld pack. The crew then moves the TRT trolley to the next weld pack on the pipeline and performs another inspection. This is processes is repeated until all CUI-susceptible locations on the particular pipeline have been inspected. Once the CUI inspections on the pipeline are complete, the inspection crew moves to the next pipeline due for CUI inspection and begins the process again. As can be seen, the TRT inspection process is very time consuming and expensive. Further, since corrosion is typically detected on only approximately 4% of inspections, much of the time and associated cost is spent inspecting CUI-susceptible locations that have not experienced detectable corrosion.

Once a sufficient degree of corrosion is detected, the original weld pack 20 is rehabilitated. FIG. 3 illustrates a rehabilitated weld pack 20' on insulated pipeline 10. To rehabilitate weld pack 20, the field-applied jacket 15 and foam insulation 16 are removed. Assuming the corrosion is detected sufficiently early, the exposed surface of the ends of pipe segments 11 and the end faces of shop-applied insulation 13 may be covered in a waterproof barrier 18 (e.g., a tape wrap, waterproof paste, etc.). Next, an oversized clamshell of insulation 16' is disposed about barrier 18 and ends of segments 11, a new field-applied jacket 15' is disposed about insulation 16', and new annular seals 17' are applied between jacket 15' and each jacket 14 to prevent moisture from reaching insulation 16' and segments 11. Due to the application of waterproof barrier 18 in rehabilitated weld pack 20', the portions of pipe segments 11 beneath shop-applied foam insulation 13 adjacent barrier 18 represent the more CUI-susceptible locations.

Accordingly, there remains a need in the art for reliable methods and devices for detecting CUI at CUI-susceptible locations along pipelines. Such methods and devices would be particularly well-received if they reduced inspection times and costs, and were adapted for use with original and rehabilitated weld packs.

BRIEF SUMMARY OF THE DISCLOSURE

These and other needs in the art are addressed in one embodiment by a method of sensing corrosion of a pipe covered by a layer of insulation. In an embodiment, the method comprises positioning a CUI sensor radially adjacent an outer surface of the pipe. The CUI sensor comprises a non-conductive base having a first end and a second end opposite the first end. In addition, the CUI sensor comprises a first test circuit mounted to the base. The first test circuit includes a first conductor, a second conductor, and a first testing element extending between the first conductor and the second conductor. Further, the method comprises exposing the first testing element to the same environment as the outer surface of the pipe. Still further, the method comprises determining whether the first testing element has corroded through. Moreover, the method comprises assessing whether corrosion of the pipe has occurred based on the determination of whether the first testing element has corroded through.

These and other needs in the art are addressed in another embodiment by a method of sensing corrosion of a pipe covered by a layer of insulation. In an embodiment, the method comprises positioning a first array of CUI sensors radially adjacent an outer surface of the pipe. Each CUI sensor in the first array comprises a non-conductive base having a first end and a second end opposite the first end and a first test circuit mounted to the base. The first test circuit includes a first conductor, a second conductor, and a first testing element extending between the first conductor and the second conductor. In addition, the method comprises exposing the first testing element of each CUI sensor in the first array to the same environment as the outer surface of the pipe. Further, the method comprises determining whether the first testing element of any of the CUI sensors in the first array has corroded through. Still further, the method comprises assessing whether corrosion of the pipe has occurred based on the determination of whether the first testing element of any of the CUIT sensors in the first array has corroded through.

These and other needs in the art are addressed in another embodiment by an array of sensors for detecting corrosion under insulation. In an embodiment, the array comprises a plurality of CUI sensors. Each CUI sensor includes a non-conductive base having a first end and a second end opposite the first end, and a first test circuit mounted to the base. The first test circuit includes a first conductor, a second conductor, a first testing element extending between the first conductor and the second conductor, and a first resistor extending between the first conductor and the second conductor in parallel with the first testing element. Each first testing element is a metal filament. The first test circuits are connected in series.

Embodiments described herein comprise a combination of features and advantages intended to address various shortcomings associated with certain prior devices, systems, and methods. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which:

FIG. 4a is a front view of an embodiment of a CUI sensor in accordance with the principles described herein;

FIG. 4b is a side view of the CUI sensor of FIG. 4a;

FIG. 6b is a side view of the CUI sensor of FIG. 6a;

FIG. 8b is a side view of the CUI sensor of FIG. 8a;

DETAILED DESCRIPTION OF THE PREFERRED EMBODIMENTS

Figure 1:
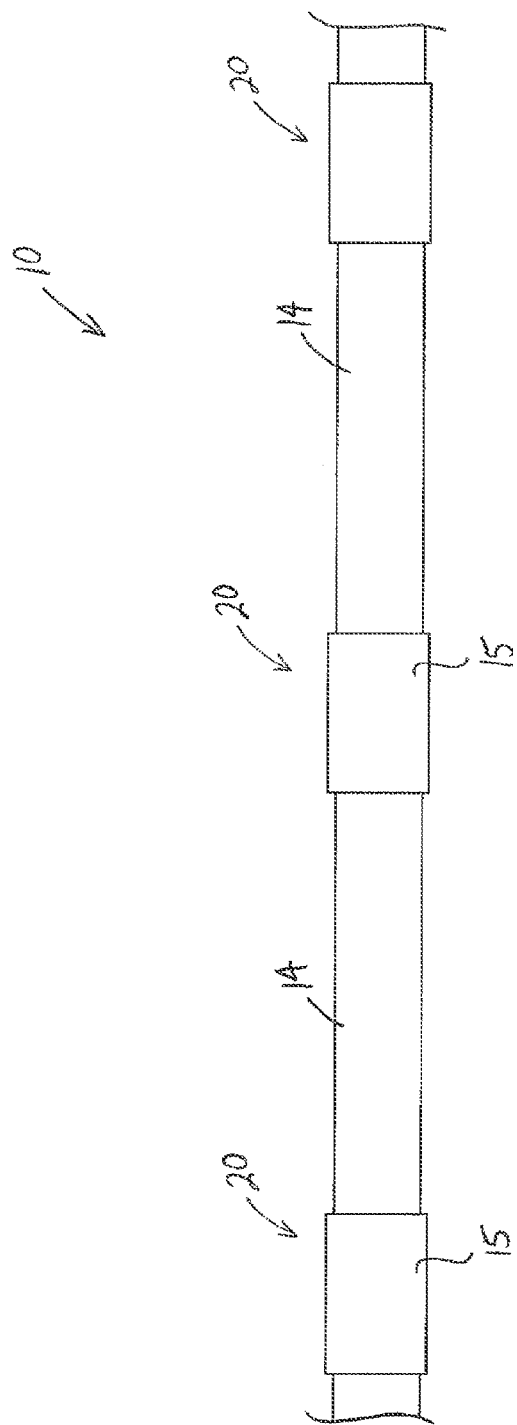
FIG. 1 is a side view of a portion of a pipeline including a plurality of weld packs.
Figure 2:
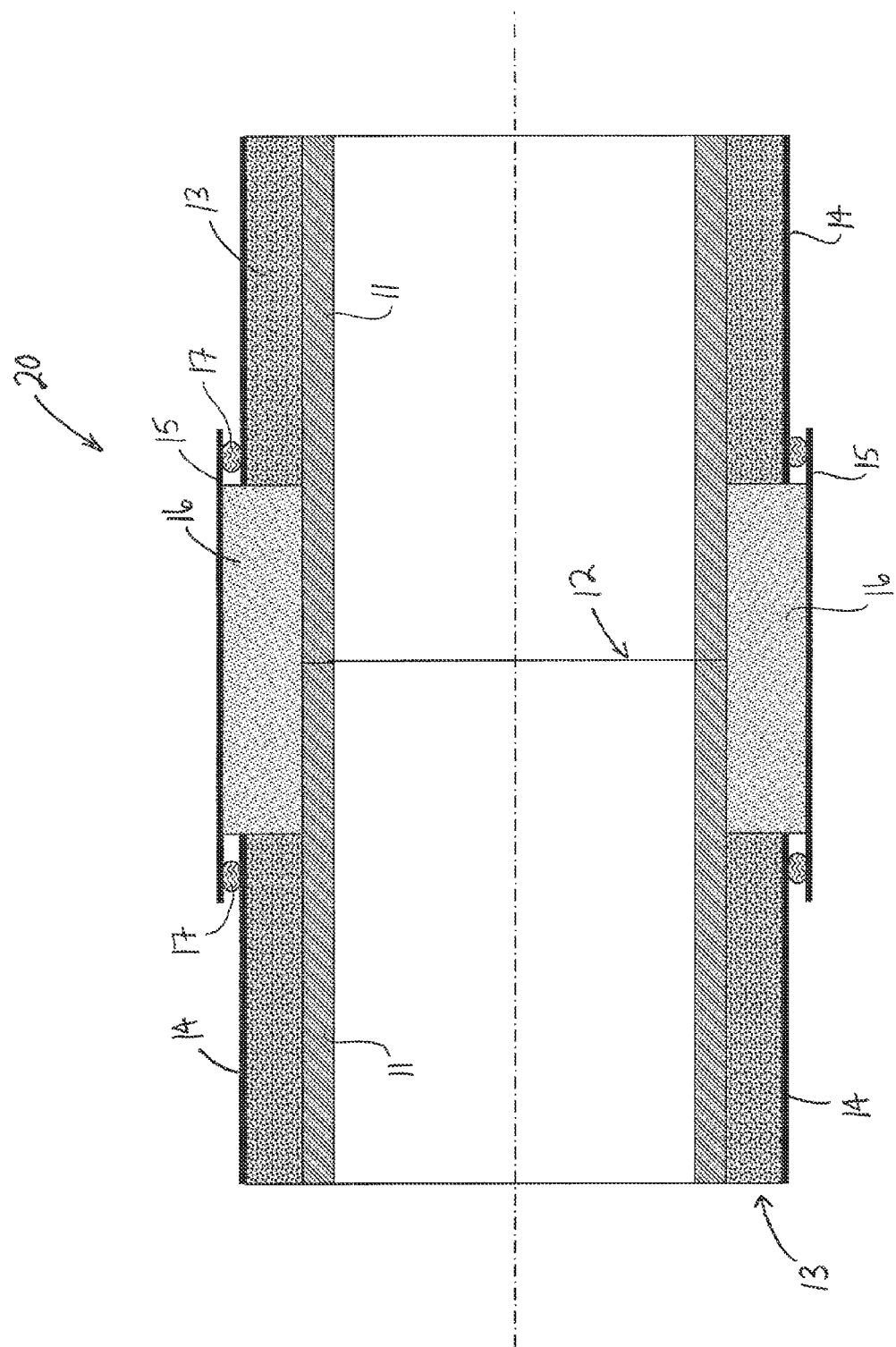
FIG. 2 is a cross-sectional view of one of the weld packs of FIG. 1.
Figure 3:
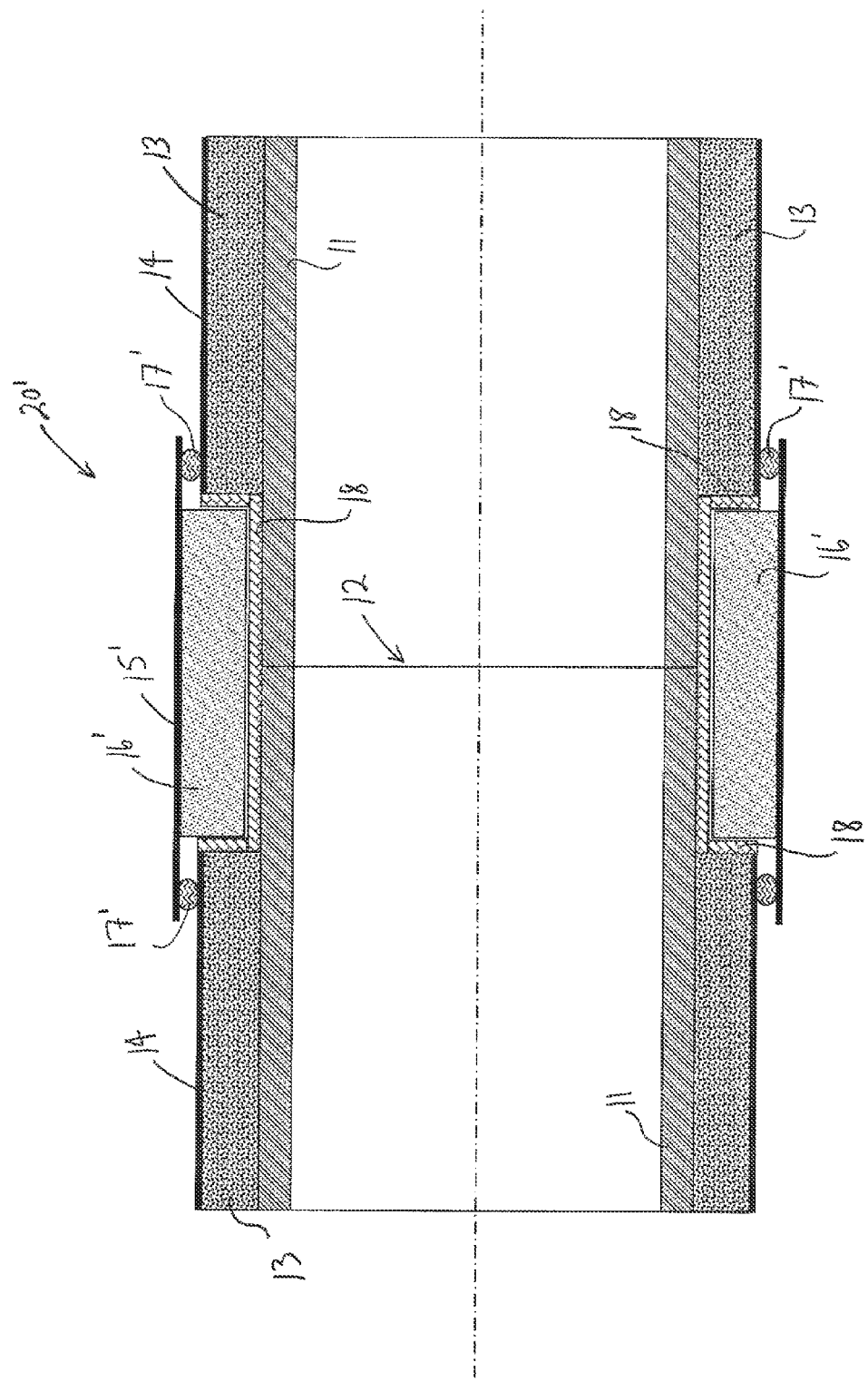
FIG. 3 is a cross-sectional view of a rehabilitated weld pack including a water-proof protective barrier.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Referring now to FIGS. 4a and 4b, an embodiment of a sensor 100 for detecting CUI is shown. In this embodiment, sensor 100 includes a substrate or base 110, a corrosion testing circuit 120 mounted to base 110, and a reference circuit 130 mounted to base 110. In general, sensor 100 is positioned adjacent a carbon steel pipe segment within an insulated pipeline to detect CUI.

Base 110 is a board having a central or longitudinal axis 115, a first end 110a, a second end 110b opposite first end 110a, and a pair of parallel lateral sides 111 extending axially between ends 110a, b. Although base 110 is shown as being rectangular in this embodiment, in general, base 110 may have any suitable geometry or shape (e.g., rectangular, curved, round, triangular, etc.). In addition, base 110 has a first or front face 112 extending axially between ends 110a, b and laterally between sides 111, and a second or rear face 113 opposite front face 112 extending axially between ends 110a, b and laterally between sides 111. As best shown in FIG. 4B, faces 112, 113 are generally parallel, planar surfaces. However, second end 110b of base 110 is beveled. In particular, second end 110b comprises a pair of flanking surfaces 114 that extend from faces 112, 113 and taper towards each other moving axially from faces 112, 113. In the side view of FIG. 4b, surfaces 114 are oriented at an acute angle relative to each other in side view, and meet at a point 116 distal faces 112, 113. As will be described in more detail below, beveled end 110b facilitates the insertion and advancement of sensor 100 through insulation (e.g., insulation 13, 16, 16').

Base 110 preferably comprises a rigid, non-conductive material such as fiberglass or a suitable plastic. In this embodiment, base 110 is a fiberglass board having a thickness measured perpendicularly between faces 112, 113 of 1/16 in.

Referring still to FIGS. 4a and 4b, testing circuit 120 is mounted to base 110 and includes a pair of electrical conductors 121, 122, and a test or testing element 124 extending between conductors 121, 122. In this embodiment, each conductor 121, 122 extends axially from a first end 121a, 122a, respectively, proximal end 110a to a second end 121b, 122b, respectively, proximal end 110b, and testing element 124 extends between ends 121b, 122b.

Reference circuit 130 is also mounted to base 110 and includes a pair of conductors 131, 122, and a reference element 134 extending between conductors 131, 122. Thus, conductor 122 is shared by testing circuit 120 and reference circuit 130. In this embodiment, each conductor 131, 122 extends axially from a first end 131a, 122a, respectively, proximal end 110a to a second end 131b, 122b, respectively, proximal end 110b, and reference element 134 extends between ends 131b, 122b. As best shown in FIG. 4a, an insulated lead or wire 101 is connected to each conductor 121, 122, 131.

In this embodiment, conductors 121, 122, 131 and elements 124, 134 comprise conductive metal strips extending along front face 112. More specifically, testing elements 124, 134 each preferably comprises the same metal, and more particular, the same material as the pipe being monitored.

Testing element 124, reference element 134, and ends 121b, 122b, 131b are positioned axially adjacent end 110b and bevel surfaces 114. Testing element 124 is exposed to the surrounding environment, however, conductors 121, 122, 131, and reference element 134 are encapsulated and sealed from the surrounding environment. In particular, reference element 134 and leads 133, 131 are coated in a non-conductive water-proof coating 140 and conductors 121, 122, 131 are embedded in a non-conductive water-proof coating 141 such as epoxy.

Figure 5:
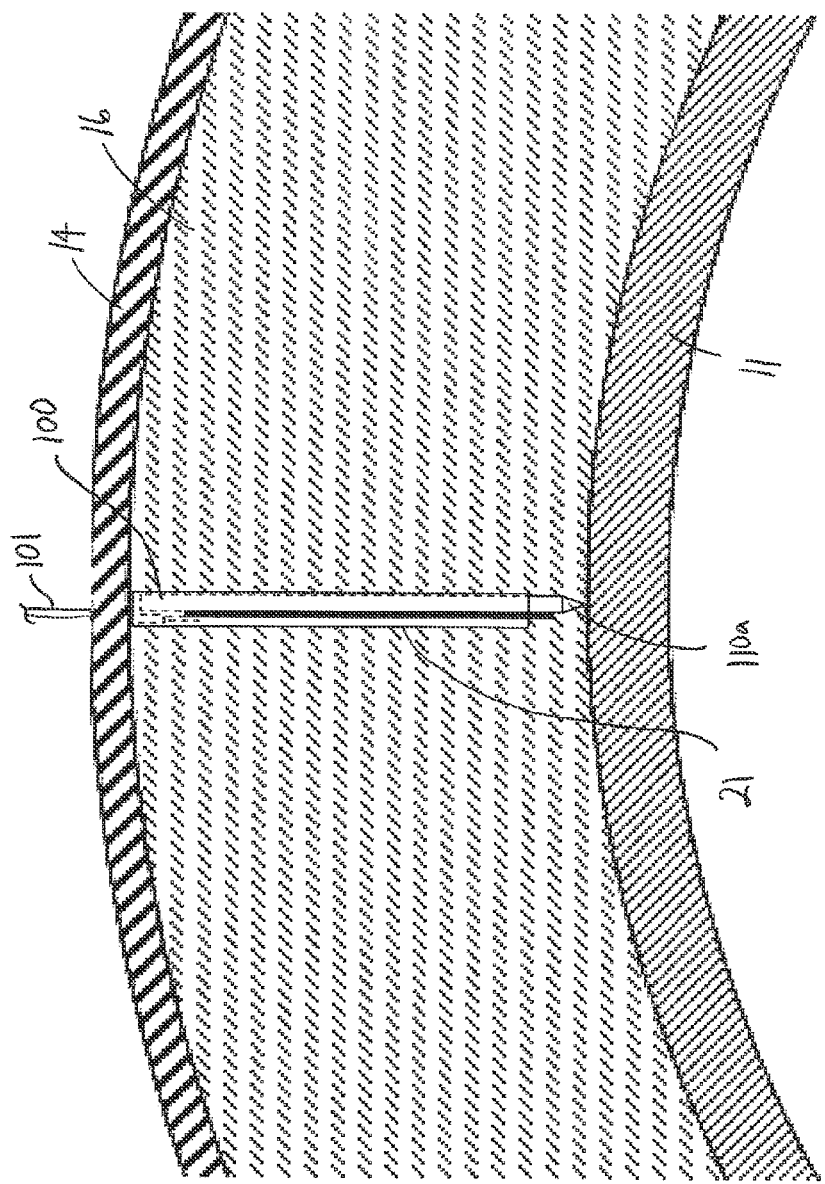
FIG. 5 is a cross-sectional end view of the weld pack of FIGS. 1 and 2 with the CUI sensor of FIG. 4a installed.

Referring now to FIG. 5, sensor 100 is shown installed in a weld pack 20 as previously described. Sensor 100 may simply be urged radially (relative to pipe segment 11) through insulation 16 with end 110b leading to form slit or gap 21 in insulation 16 as it advances therethrough 16. Sensor 100 is preferably radially advanced through insulation 16 until end 110b touches segment 11. As a result, elements 124, 134 are positioned radially proximate pipe segment 11. Alternatively, gap 21 may be preformed, and then end 110b is inserted into gap 21 and sensor 100 is pushed into gap 21 until end 110b touches segment 11. However, whether gap 21 is preformed in insulation 16 or formed by advancing sensor 100 through insulation 16, testing element 124 directly engages insulation 16, and coating 140 on reference element 134 directly engages insulation 16. This ensures testing element 124 experiences the same or substantially the same environment (e.g., temperature, wetness, etc.) as segment 11, and ensures reference element 134 experiences the same or substantially the same environment as segment 11 with the exception that element 134 is protected from moisture by coating 140.

Leads 101 extending from conductors 121, 122, 131 are routed through a seal 17 or through jacket 15 to the environment outside weld pack 20 so that they can be easily accessed. Regardless of the exit point of wires 101, a seal is preferably formed around each lead 101 to restrict and/or prevent moisture from passing through seal 17 or jacket 15.

Since element 124 is not coated or covered, it is exposed to the same environment (e.g., temperature and wetness) as pipe segment 11. Further, since element 124 is made from the same material as pipe segment 11, and is exposed to the same environment as pipe segment 11, it functions as a corrosion proxy for segment 11. In other words, corrosion of testing element 124 is an indicator that corresponding pipe segment 11 is corroding.

The corrosion of testing element 124, and hence the corrosion of pipe segment 11, is detected by measuring and comparing the resistance across elements 124, 134, with reference element 134 serving as a baseline to account for small differences in resistance due to temperature changes. In particular, using a meter (e.g., multimeter or ohmmeter), a voltage differential is applied across conductors 121, 122 and the current flowing through circuit 120 is measured, and then the same voltage differential is applied across conductors 131, 122 and the current flowing through circuit 130 is measured. Using the voltage differential applied across conductors 121, 122 and the measured current in testing circuit 120, the meter determines the resistance across test element 124; and using the voltage differential applied across conductors 122, 131 and the measured current in reference circuit 130, the meter determines the resistance across reference element 134. If there has been little corrosion of element 124, the resistance across elements 124, 134 should be the same, each being about very small (~0 ohms), thereby indicating that pipe segment 11 has experienced little corrosion. However, if there has been corrosion of testing element 124, the resistance across element 124 will be different than the resistance across element 134, thereby indicating that pipe segment 11 has experienced corrosion. In general, the greater the corrosion of element 124, the greater the resistance across conductors 121, 122. Therefore, a significantly large resistance across element 124 indicates it has corroded completely through, resulting in testing circuit 120 essentially functioning like an open circuit.

In this embodiment, CUI sensor 100 is not specifically tailored to indicate a particular corrosion rate, but rather, indicate whether a predetermined amount of corrosion of pipe segment 11 has occurred. In particular, the thickness of testing element 124 may be varied to identify when specific amount of corrosion has occurred. For example, if testing element 124 is 10 mils thick, when it is determined from resistance measurements that element 124 has corroded through, it would indicate that at least 10 mils of corrosion occurred on testing element 124 and presumably on corresponding pipe segment 11.

In the manner previously described, whether testing element 124 has corroded is determined by a change in resistance across testing element 120 relative to the resistance across reference element 134, and not just checking for an open circuit. Thus, when testing element 124 becomes wet, it will corrode. However, even if element 124 has corroded through, if element 124 is still wet, testing circuit 120 will not be a true open circuit, especially if the water is somewhat saline. However, there will be a significant change in resistance across element 124 relative to the measured resistance across element 134, which will be detectable regardless of whether testing element 124 is wet or dry a the time the measurement is made.

Figure 6B:
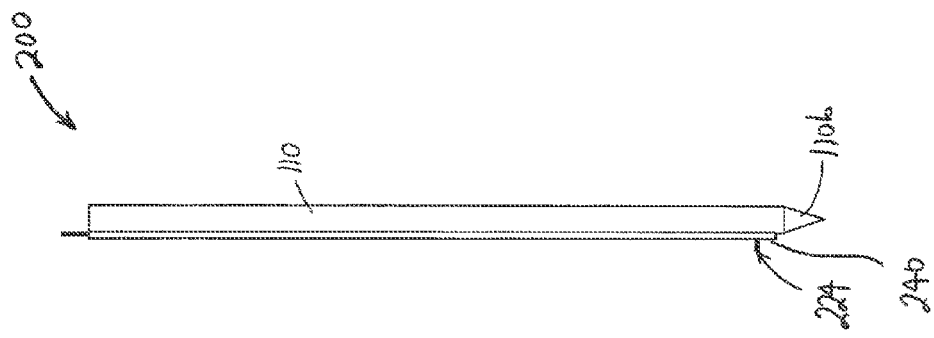
Figure 6A:
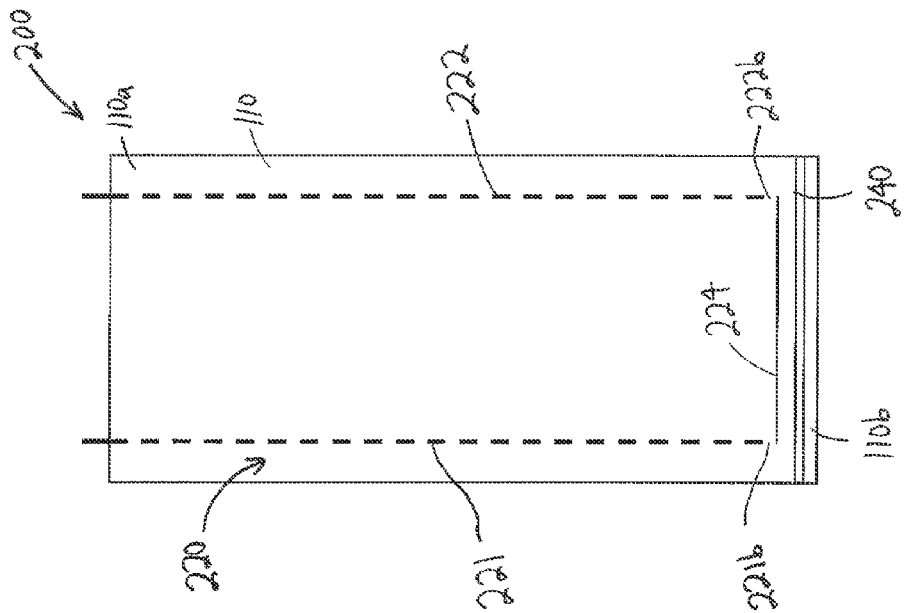
FIG. 6a is a front view of an embodiment of a CUI sensor in accordance with the principles described herein.

Referring now to FIGS. 6a and 6b, an embodiment of a sensor 200 for detecting CUI is shown. In this embodiment, sensor 200 includes a base 110 as previously described and a corrosion testing circuit 220 mounted to base 110. In general, sensor 200 is positioned proximal to a carbon steel pipe within the thermal insulation to detect CUI.

Testing circuit 220 is mounted to base 110 and includes a pair of electrical conductors 221, 222, and a testing element 224 extending between conductors 221, 222 adjacent end 110b. In this embodiment, each conductor 221, 222 extends axially (relative to base axis 115) from end 110a to a lower end 221b, 222b, respectively, proximal end 110b. Conductors 221, 222 extend along face 112 and are covered with a non-conductive water-proof layer or coating 240 such as a fiberglass laminate, however, ends 221b, 222b extend from base 110 through layer 240, and testing element 224 is disposed outside layer 240. In other words, testing element 240 is completely exposed to the environment around sensor 200. In this embodiment, conductors 221, 222 comprise wires extending along face 112, and testing element 224 comprises a metal filament made from the same material as the pipe segment being monitored (e.g., carbon steel) and preferably having a diameter between 2 mil and 100 mil, and more preferably between 5 mil and 20 mil. In this embodiment, element 224 has a diameter of 10 mil. As will be described in more detail below, in other embodiments, sensor 200 may be formed as printed circuit board (PCB) with base 110 comprising the board and conductors 221, 222 being traces or printed wires on the PCB.

Figure 7:
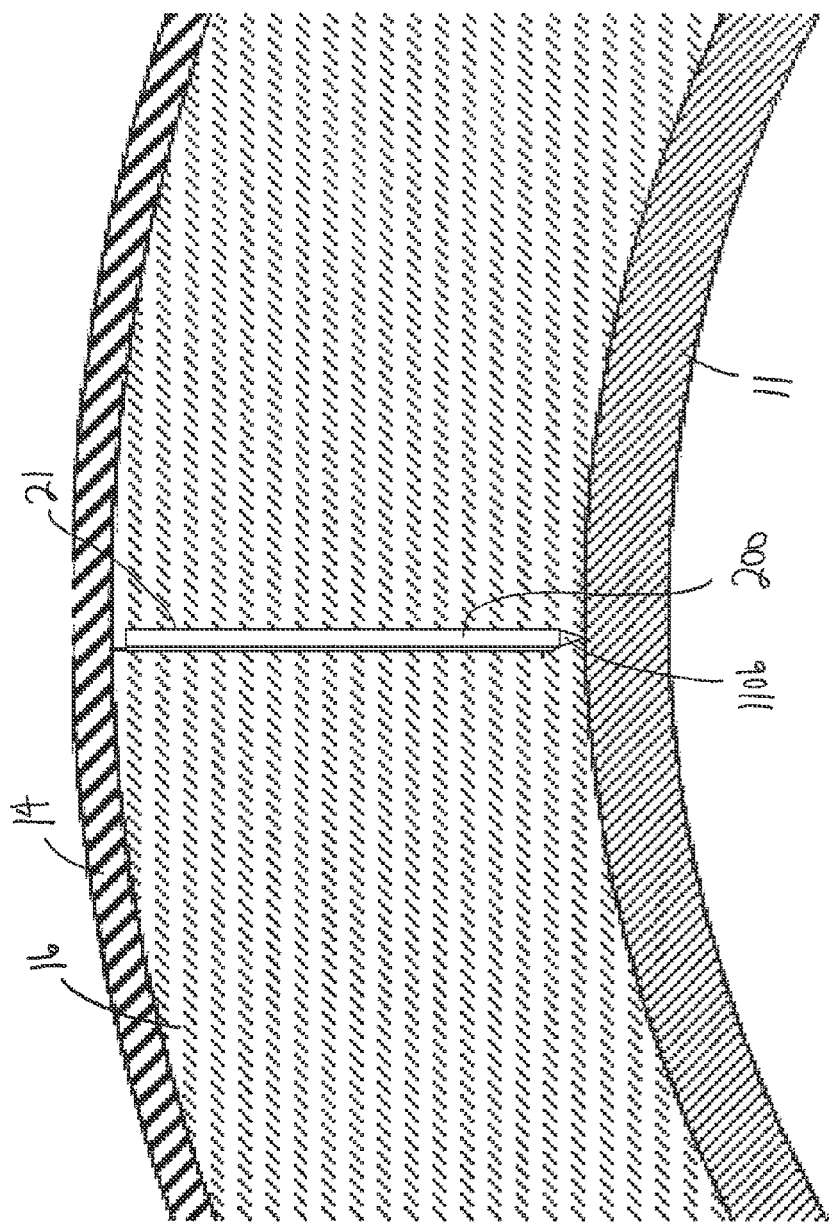
FIG. 7 is a cross-sectional end view of the weld pack of FIGS. 1 and 2 with the CUI sensor of FIG. 6a installed.

Referring now to FIG. 7, sensor 200 is installed in weld pack 20 in the same manner as sensor 100 previously described. Namely, sensor 200 is pushed through insulation 16 until end 110b touches segment 11. As a result, element 224 is in direct contact with insulation 16 radially proximate pipe segment 11. Conductors 221, 222 extending from upper end 110a are routed through seal 17 or through jacket 15 to the environment outside weld pack 20 so that they can be easily accessed. Regardless of the exit point of conductors 221, 222, a seal is preferably formed around each conductor 221, 222 to restrict and/or prevent moisture from passing through seal 17 or jacket 15.

Since element 224 is not coated or covered with layer 240, it will experience the same environment (e.g., temperature and wetness) as pipe segment 11. Further, since element 224 is made from the same material as pipe segment 11, and is exposed to the same environment as pipe segment 11, it functions as a corrosion proxy for segment 11. In other words, corrosion of testing element 224 is an indicator that corresponding pipe segment 11 is corroding (and vice versa).

The corrosion of testing element 224, and hence the corrosion of pipe segment 11, is detected by determining the resistance across element 224. In particular, using a meter (e.g., multimeter or ohmmeter), a voltage differential is applied across conductors 221, 222 and the current flowing through circuit 220 is measured. Using the voltage differential applied across conductors 221, 222 and the measured current in testing circuit 220, the meter determines the resistance across test element 224. If there has been little corrosion of element 224, the resistance across element 224 will be about ~0 ohms (i.e., testing circuit 220 is a closed circuit), thereby indicating that pipe segment 11 has experienced little corrosion. However, once element 224 has corroded completely through, the resistance across element 224 will be significantly large resulting in testing circuit 120 essentially functioning like an open circuit.

Although only one sensor 200 is shown in FIG. 7, in other embodiments, a plurality of sensors 200 may be installed in a weld pack 20 to monitor and detect corrosion at multiple locations along pipe segments 11. In such embodiments, a meter may be used by the inspector to determine the resistance across element 224 of each sensor 200 as previously described.

In this embodiment, CUI sensor 200 is not specifically tailored to indicate a particular corrosion rate, but rather, indicate whether a predetermined amount of corrosion of pipe segment 11 has occurred. In particular, the thickness of testing element 224 may be varied to identify when specific amount of corrosion has occurred. For example, if testing element 224 is 10 mils thick, when it is determined from resistance measurements that element 224 has corroded through, it would indicate that at least 10 mils of corrosion occurred on testing element 224 and presumably on corresponding pipe segment 11.

Figure 8B:
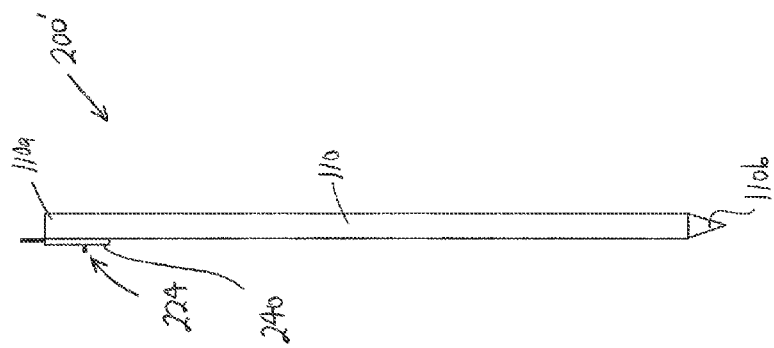
Figure 8A:
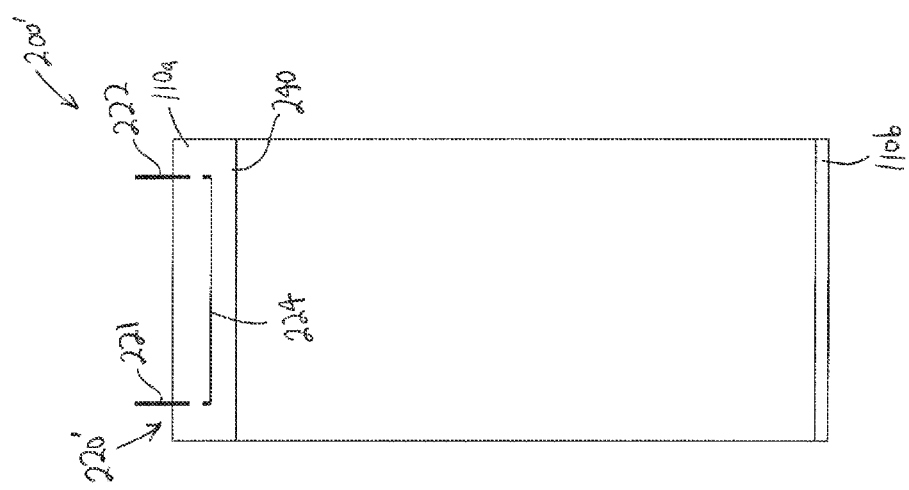
FIG. 8a is a front view of an embodiment of a CUI sensor in accordance with the principles described herein.

Referring now to FIGS. 8a and 8b, an embodiment of a sensor 200' for detecting CUI is shown. Sensor 200' is the same as sensor 200 previously described with the exception that testing element 224 is positioned axially adjacent end 110a (i.e., distal end 110b). In particular, sensor 200' comprises base 110 and a testing circuit 220' mounted to base 110. Testing circuit 220' includes conductors 221, 222 and testing element 224 extending between conductors 221, 222 proximal end 110a, each as previously described.

Figure 9:
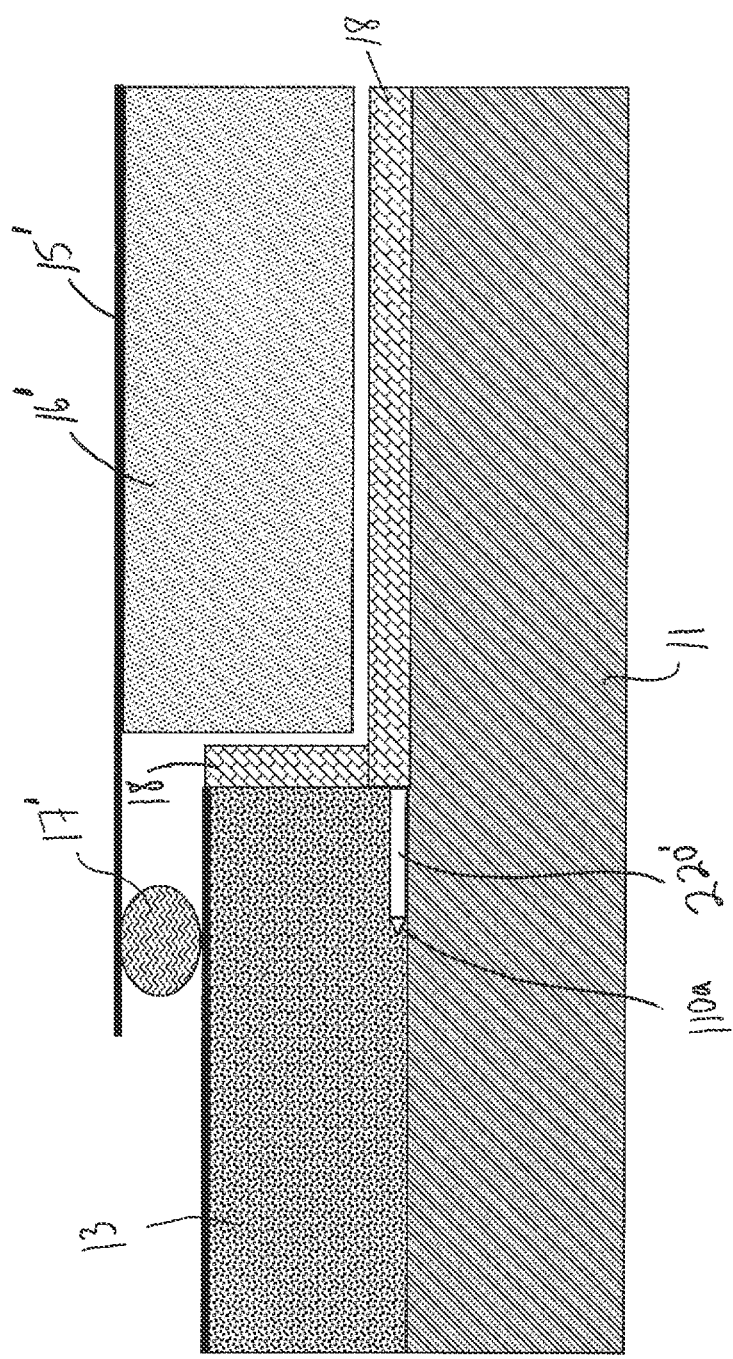
FIG. 9 is a cross-sectional end view of the weld pack of FIG. 3 with the CUI sensor of FIG. 8a installed.

This configuration is preferred for use with rehabilitated weld pack 20' previously described. In particular, positioning of element 224 proximal the leading end 110b of base 110 in sensor 200 previously described enables element 224 to be located adjacent pipe segment 11 when sensor 200 is radially inserted into gap 21. However, for rehabilitated weld pack 20', barrier 18 protects the ends of pipe segments 11, and thus, the most CUI susceptible area of pipe segment 11 is beneath shop-applied insulation 13 axially adjacent barrier 18. Thus, as shown in FIG. 9, for rehabilitated weld pack 20', testing element 224 is preferably positioned between insulation 13 and pipe segment 11 axially adjacent barrier 18 as shown in FIG. 9. In particular, after removal of field-applied steel jacket 15 and foam insulation 16, and before application of barrier 18, end 110b is inserted between insulation 13 and pipe segment 11, and sensor 200' is wedged axially therebetween. As a result, element 224 (being positioned proximal end 110a) directly contacts insulation 13 radially adjacent pipe segment 11 and axially adjacent the end face of insulation 13. Next, barrier 18, insulation 16', and jacket 15' are installed. Conductors 221, 222 extending from end 110a are routed between the end face of insulation 13 and barrier 18 and through seal 17 or through jacket 15 to the environment outside weld pack 20 so that they can be easily accessed. Regardless of the exit point of conductors 221, 222, a seal is preferably formed around each conductor 221, 222 to restrict and/or prevent moisture from passing through seal 17 or jacket 15. Once installed, sensor 200' is operated in the same manner as sensor 200 previously described.

Although only one sensor 200' is shown in FIG. 9, in other embodiments, a plurality of sensors 200' may be installed in a weld pack 20' to monitor and detect corrosion at multiple locations along pipe segments 11. In such embodiments, a meter may be used by the inspector to determine the resistance across element 224 of each sensor 200' as previously described.

Figure 10:
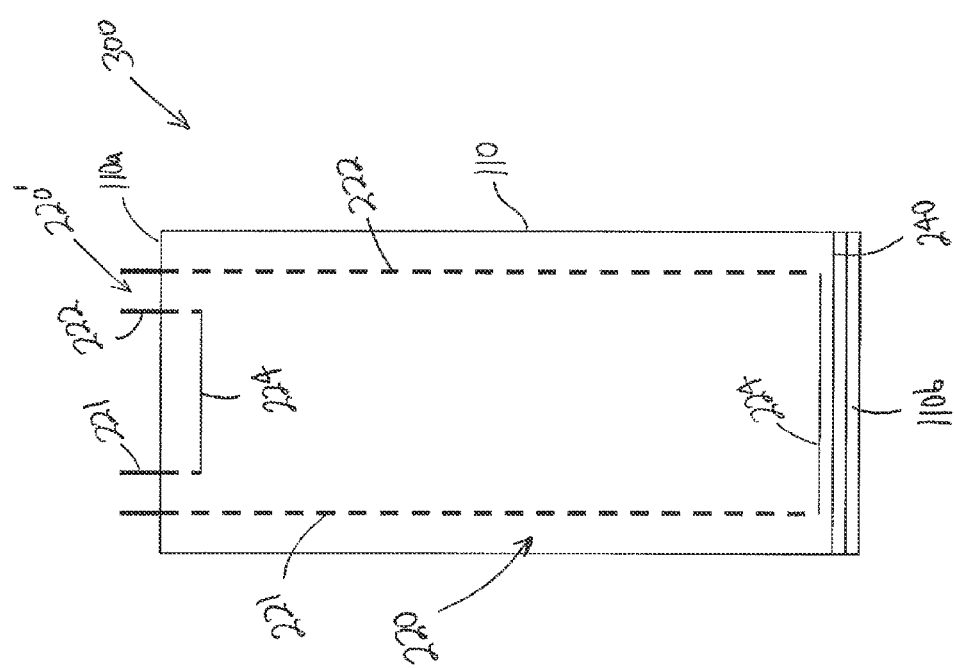
FIG. 10 is a front view of an embodiment of a CUI sensor in accordance with the principles described herein.

Referring now to FIG. 10, an embodiment of a sensor 300 for detecting CUI is shown. In this embodiment, sensor 300 includes base 110, one testing circuit 220, and one testing circuit 220', each as previously described. Thus, in this embodiment, one exposed element 224 is positioned axially adjacent end 110b (i.e., distal end 110a) and the other exposed element 224 is positioned axially adjacent end 110a (i.e., distal end 110b). A meter may be used to determine the resistance of either circuit 220, 220' in the same manner as previously described to assess corrosion of either element 224.

Inclusion of both testing circuits 220, 220' enhances the versatility of sensor 300. More specifically, one or more sensors 300 may be installed in the same manner as sensor 200 previously and used to detect corrosion in an original weld pack 20 (i.e., with element 224 at end 110b positioned radially adjacent pipe segment 11), or installed in the same manner as sensor 200' and used to detect corrosion in a rehabilitated weld pack 20' (i.e., with element 224 at end 110a positioned radially adjacent pipe segment 11 and axially adjacent barrier 18).

It should also be appreciated that inclusion of two testing circuits 220, 220' may be used to detect the ingress of moisture into insulation 13, 16. For example, if sensor 300 is installed in the same manner as sensor 200 (FIG. 7), elements 224 may be used to detect the radial movement of moisture through insulation 16. In particular, corrosion of element 224 at end 110a may be used to detect moisture ingress along the radially outer portion of insulation 16 and corrosion of element 224 at end 110b may be used to detect moisture ingress along the radially inner portion of insulation 16 adjacent pipe segment 11. As another example, if sensor 300 is installed in the same manner as sensor 200' (FIG. 9), elements 224, 224 may be used to detect the axial movement of moisture along pipe segment 11 through insulation 13. In particular, corrosion of element 224 at end 110a may be used to detect moisture ingress along pipe segment 11 axially adjacent barrier 18 and corrosion of element 224 at end 110*b* may be used to detect moisture ingress along pipe segment 11 axially distal barrier 18.

Figure 11:
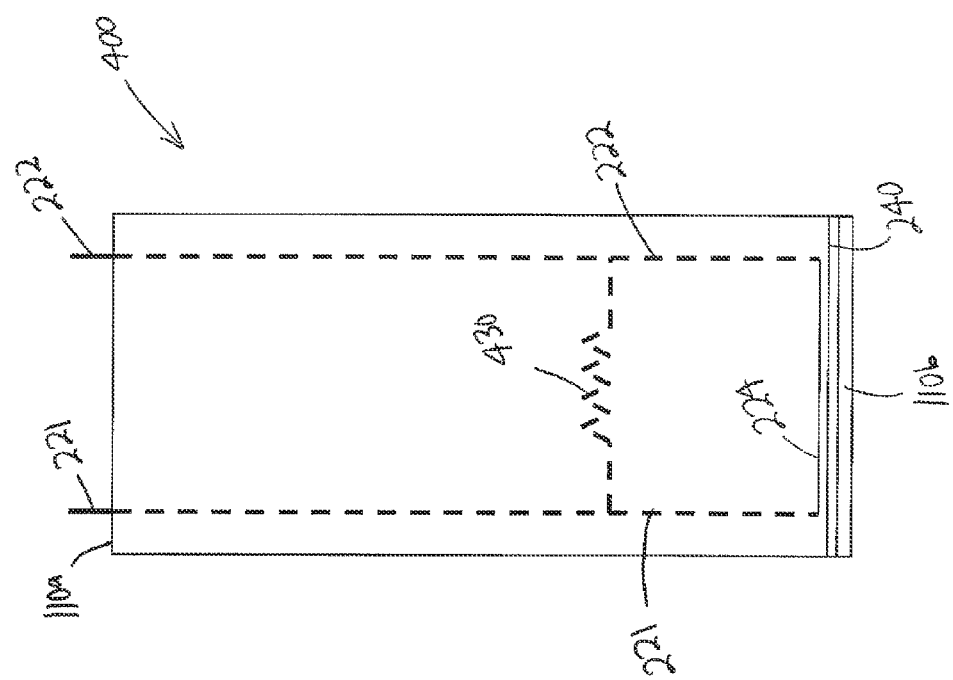
FIG. 11 is a front view of an embodiment of a CUI sensor in accordance with the principles described herein.

Referring now to FIG. 11, another embodiment of a sensor 400 for detecting CUI is shown. Sensor 400 is the same as sensor 200 previously described with the exception that sensor 400 includes a reference resistor 430 extending between conductors 221, 222 and in parallel with element 224. In particular, sensor 400 comprises base 110 and a testing circuit 420 mounted to base 110. Testing circuit 420 includes conductors 221, 222, testing element 224 extending between conductors 221, 222, and reference resistor 430 extending between conductors 221, 222 and in parallel with element 224. Resistor 430 is preferably positioned between base 110 and layer 240 to protect resistor 430 from corrosion.

One or more sensors 400 may be installed in the same manner as sensor 200 previously described. As a result, element 224 is positioned radially proximate pipe segment 11. The corrosion of testing element 224, and hence the corrosion of pipe segment 11, is detected using a meter as previously described (i.e., by applying a voltage differential across conductors 221, 222 and measuring the associated current to determine the resistance between conductors 221, 222). If there has been little to no corrosion of element 224, the resistance across element 224 will be about ~0 ohms (i.e., element 224 is a short between conductors 221, 222), thereby indicating that pipe segment 11 has experienced little corrosion. However, once element 224 has corroded completely through, the resistance across element 224 will be significantly greater than the resistance across reference resistor 430, and thus, the resistance determined by the meter will be the resistance of reference resistor 430.

Figure 12:
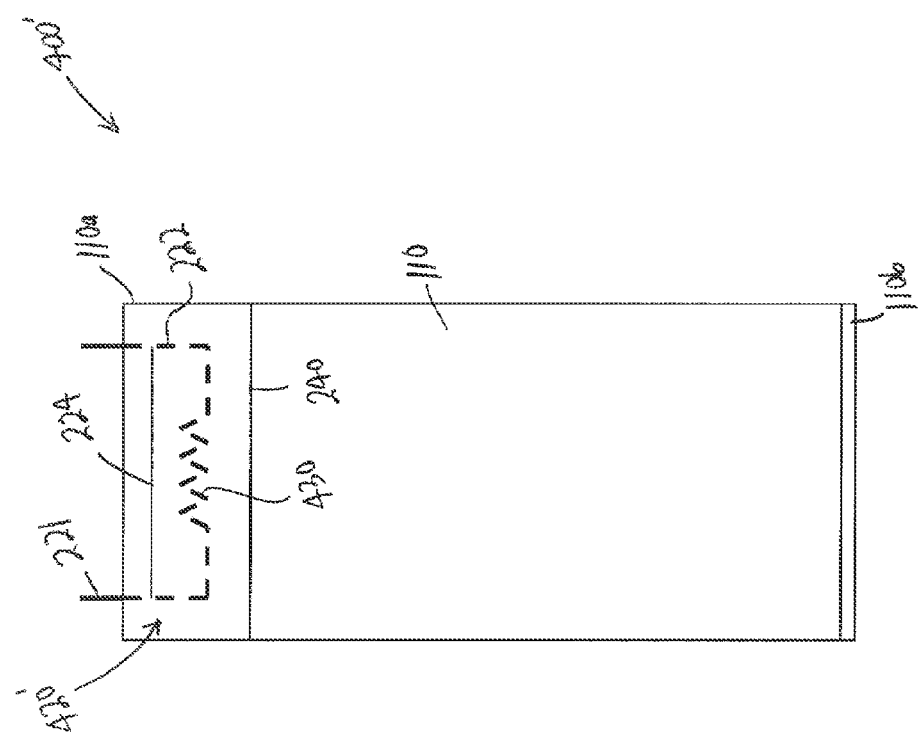
FIG. 12 is a front view of an embodiment of a CUI sensor in accordance with the principles described herein.

Referring now to FIG. 12, an embodiment of a sensor 400' for detecting CUI is shown. Sensor 400' is the same as sensor 400 previously described with the exception that testing element 224 is positioned axially adjacent end 110*a* (i.e., distal end 110*b*). In particular, sensor 400' comprises base 110 and a testing circuit 420' mounted to base 110. Testing circuit 420' includes conductors 221, 222, testing element 224 extending between conductors 221, 222 proximal end 110*a*, and reference resistor 430 extending between conductors 221, 222 and in parallel with element 224, each as previously described.

This configuration is preferred for use with rehabilitated weld pack 20'. As previously described, for a rehabilitated weld pack 20', barrier 18 protects the ends of pipe segments 11, and thus, the most CUI susceptible area of pipe segment 11 is beneath shop-applied insulation 13 axially adjacent barrier 18. Thus, for rehabilitated weld pack 20', testing element 224 is preferably positioned between insulation 13 and pipe segment 11 axially adjacent barrier 18 as shown in FIG. 9. After removal of field-applied steel jacket 15 and foam insulation 16, and before application of barrier 18, end 110*b* is inserted between insulation 13 and pipe segment 11, and sensor 400' is wedged axially therebetween. As a result, element 224 (being positioned proximal end 110*a*) is positioned radially adjacent pipe segment 11 and axially adjacent the end face of insulation 13. Next, barrier 18, insulation 16', and jacket 15' are installed. Conductors 221, 222 extending from end 110*a* are routed between the end face of insulation 13 and barrier 18 and through seal 17 or through jacket 15 to the environment outside weld pack 20 so that they can be easily accessed. Regardless of the exit point of conductors 221, 222, a seal is preferably formed around each conductor 221, 222 to restrict and/or prevent moisture from passing through seal 17 or jacket 15. Once installed, sensor 400' is operated in the same manner as sensor 400 previously described.

Although installation of only one sensor 400' is described, a plurality of sensors 400' may be installed in a weld pack 20' to monitor and detect corrosion at multiple locations along pipe segments 11. In such embodiments, a meter may be used by the inspector to determine the resistance across element 224 of each sensor 400' as previously described.

Figure 13:
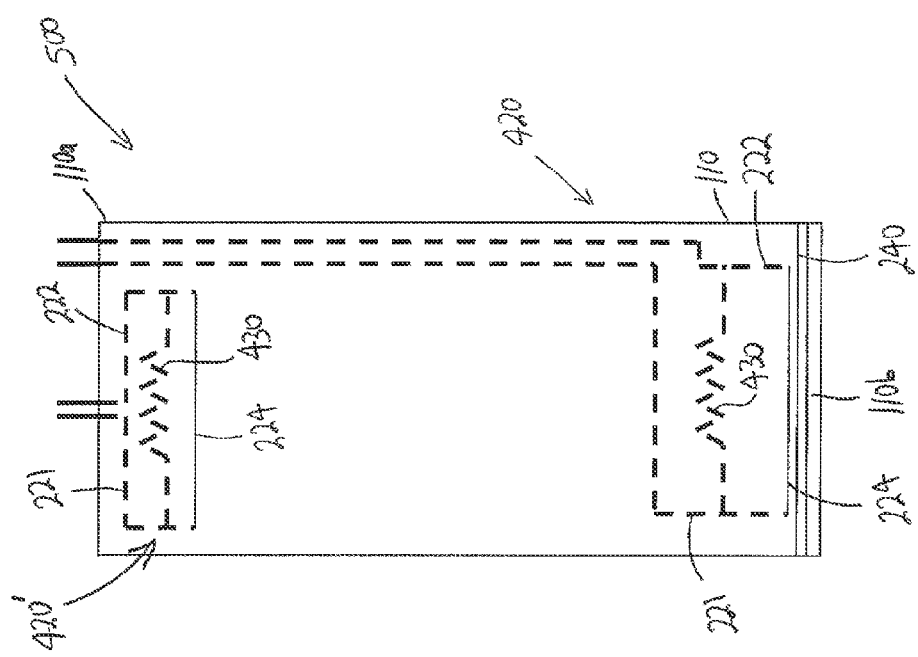
FIG. 13 is a front view of an embodiment of a CUI sensor in accordance with the principles described herein.

Referring now to FIG. 13, an embodiment of a sensor 500 for detecting CUI is shown. In this embodiment, sensor 500 includes base 110, one testing circuit 420, and one testing circuit 420', each as previously described. Thus, in this embodiment, one element 224 is positioned axially adjacent end 110*b* (i.e., distal end 110*a*) and the other element 224 is positioned axially adjacent end 110*a* (i.e., distal end 110*b*). A meter may be used to determine the resistance of either circuit 420, 420' in the same manner as previously described to assess corrosion of either element 224.

Inclusion of both testing circuits 420, 420' enhances the versatility of sensor 500. More specifically, one or more sensors 500 may be installed in the same manner as sensor 200 previously and used to detect corrosion in an original weld pack 20 (i.e., with element 224 at end 110*b* positioned radially adjacent pipe segment 11), or installed in the same manner as sensor 200' and used to detect corrosion in a rehabilitated weld pack 20' (i.e., with element 224 at end 110*a* positioned radially adjacent pipe segment 11 and axially adjacent barrier 18).

It should also be appreciated that inclusion of two testing circuits 420, 420' may be used to detect the ingress of moisture into insulation 13, 16. For example, if sensor 500 is installed in the same manner as sensor 200 (FIG. 7), elements 224, 224 may be used to detect the radial movement of moisture through insulation 16. In particular, corrosion of element 224 at end 110*a* may be used to detect moisture ingress along the radially outer portion of insulation 16 and corrosion of element 224 at end 110*b* may be used to detect moisture ingress along the radially inner portion of insulation 16 adjacent pipe segment 11. As another example, if sensor 500 is installed in the same manner as sensor 200' (FIG. 9), elements 224, 224 may be used to detect the axial movement of moisture along pipe segment 11 through insulation 13. In particular, corrosion of element 224 at end 110*a* may be used to detect moisture ingress along pipe segment 11 axially adjacent barrier 18 and corrosion of element 224 at end 110*b* may be used to detect moisture ingress along pipe segment 11 axially distal barrier 18.

Figure 14:
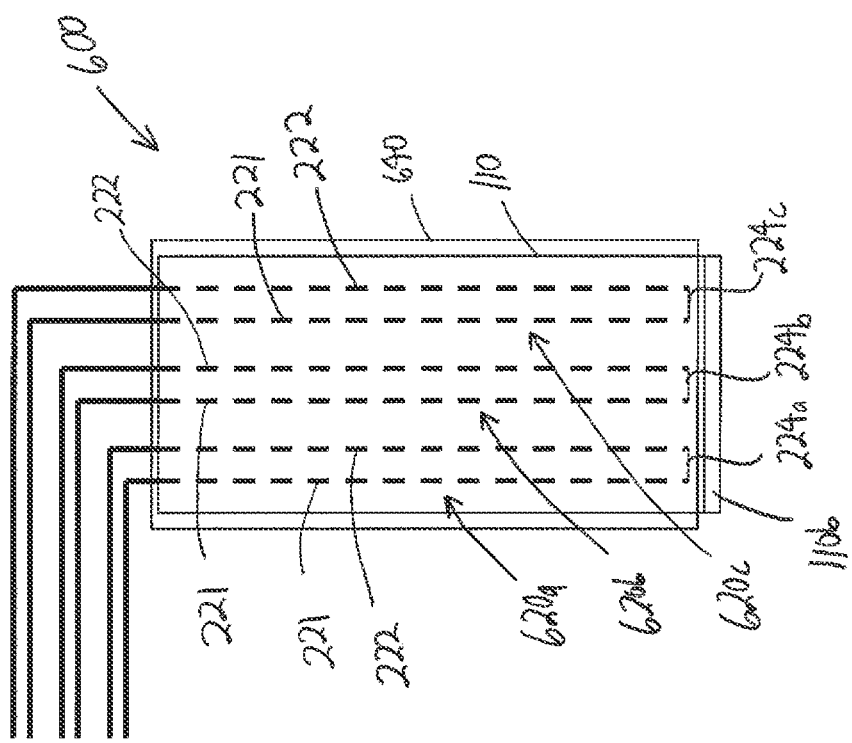
FIG. 14 is a front view of an embodiment of a CUI sensor in accordance with the principles described herein.

Referring now to FIG. 14, an embodiment of a sensor 600 for detecting CUI is shown. In this embodiment, sensor 600 includes a base 110 as previously described and a plurality of corrosion testing circuits 620*a, b, c* mounted to base 110. In general, sensor 600 is positioned proximal a steel pipe segment within an insulated pipeline to detect CUI.

Each testing circuit 620*a, b, c* is similar to testing circuit 220 previously described. Namely, each testing circuit 620*a, b, c* includes a pair of conductors 221, 222 and a test or testing element 224*a, b, c*, respectively, extending between conductors 221, 222. Each testing element 224*a, b, c* is the same as testing element 224 previously described. Further, in this embodiment, each testing element 224*a, b, c* is positioned axially adjacent end 110*b*, however, in other embodiments, one or more elements 224*a, b, c* may be positioned proximal end 110*a*. Conductors 221, 222 extend axially along base 110 and are covered with a non-conductive water-proof layer or coating 640 such as a fiberglass laminate, however, each testing element 224*a, b, c* is disposed outside layer 640. In other words, each testing element 224*a, b, c* is completely exposed to the environment around sensor 600. The diameter of each testing element 224*a, b, c* may be between about 2 mil and about 100 mil, and alternatively between about 5 mil and about 20 mil. For example, element 224a may have a diameter of 5 mil, element 224b may have a diameter of 10 mil, and element 224c may have a diameter of 20 mil. However, in general, testing elements 224a, b, and c may be of any suitable diameter.

One or more sensors 600 are installed in weld pack 20 in the same manner as sensor 200 previously described and shown in FIG. 7. Namely, end 110b is inserted into gap 21 and sensor 600 is pushed into gap 21 until end 110b touches segment 11. As a result, each element 224a, b, c is positioned radially adjacent pipe segment 11. Conductors 221, 222 extending from upper end 110a are routed through seal 17 or through jacket 15 to the environment outside weld pack 20 so that they can be easily accessed. Regardless of the exit point of conductors 221, 222, a seal is preferably formed around each conductor 221, 222 to restrict and/or prevent moisture from passing through seal 17 or jacket 15. In embodiments where elements 224a, b, c are positioned proximal end 110a, the sensor (e.g., sensor 600) is preferably installed in weld pack 20' in the same manner as sensor 200' previously described and shown in FIG. 7.

Since elements 224a, b, c are not coated or covered with layer 640, each will experience the same environment (e.g., temperature and wetness) as pipe segment 11. Further, since each element 224a, b, c is made from the same material as pipe segment 11, and is exposed to the same environment as pipe segment 11, it functions as a corrosion proxy for segment 11. In other words, corrosion of testing elements 224a, b, c is an indicator that corresponding pipe segment 11 is corroding.

The corrosion of each testing element 224a, b, c, and hence the corrosion of pipe segment 11, is detected by determining the resistance across each element 224a, b, c using the corresponding conductors 221, 222 as previously described (i.e., by applying a voltage differential across each pair of conductors 221, 222 and measuring the associated current to determine the resistance of each element 224a, b, c). If there has been little corrosion of an element 224a, b, c, the resistance across that particular element 224a, b, c will be very low (~0 ohms)—the corresponding testing circuit 620a, b, c functioning like a closed circuit. However, once a particular element 224a, b, c has corroded completely through, the resistance across that element 224a, b, c will be significantly large—the corresponding testing circuit 620a, b, c essentially functioning like an open circuit. By employing different diameter elements 224a, b, c, a degree of corrosion and a rate of corrosion can be estimated. For instance, using the example above in which element 224a has a diameter of 5 mil, element 224b has a diameter of 10 mil, and element 224c has a diameter of 20 mil, and assuming each element 224a, b, c experiences the same or substantially the same environment as each other and the corresponding pipe segment 11, element 224a will corrode completely through before elements 224b, c, and element 224b will corrode completely through before element 224c since element 224a is thinner than elements 224b, c and element 224b is thinner than element 224c. Accordingly, when the resistance across element 224a indicates element 224a has not corroded completely through, corrosion of the portion of the corresponding pipe segment 11 adjacent sensor 600 can be estimated to be less than 5 mil; when the resistance across element 224a indicates element 224a has corroded completely through, but the resistance across element 224b indicates element 224b has not corroded completely through, corrosion of the portion of the corresponding pipe segment 11 adjacent sensor 600 can be estimated to be somewhere between about 5 mil and 10 mil; when the resistance across element 224b indicates element 224b has corroded completely through, but the resistance across element 224c indicates element 224c has not corroded completely through, corrosion of the portion of the corresponding pipe segment 11 adjacent sensor 600 can be estimated to be somewhere between about 10 mil and 20 mil; and when the resistance across element 224c indicates element 224c has corroded completely through, corrosion of the portion of the corresponding pipe segment 11 adjacent sensor 600 can be estimated to be greater than 20 mil.

Moreover, when the corrosion of elements 224a, b, c are tracked over time, corrosion rates can be estimated. For example, when sensor 600 is initially installed, it may be assumed that corrosion has not yet initiated. The first indication of corrosion occurs when element 224a corrodes completely through. However, since it is unclear when the corrosion actually began, a corrosion rate may not yet be estimated. However, once element 224a corrodes completely through, subsequent corrosion of elements 224b, c may be used to estimate a corrosion rate. For example, if element 224b corrodes completely through over the next year, the estimated corrosion rate over that half year is about 5 mil per year (5 mil/1 year assuming 5 mil of element 224b corroded along with element 224a and the additional 5 mil of element 224b corroded during the next year).

In each of the embodiments previously described (e.g., sensors 100, 200, 200', 300, 400, 400', 500, 600), the testing circuits and reference circuits (if any) are mounted to base 110, which is generally described as a rigid non-conductive water-proof board such as a fiberglass board. In addition, the circuits on the base 110, except for the testing elements, are covered with a non-conductive water-proof coating or layer (e.g., fiberglass laminate or epoxy coating). In sensor 100, conductors 121, 122, 131 are metal strips, and in sensors 200, 200', 300, 400, 400', 500, 600, conductors 221, 222 are insulated wires. The metal strips in sensor 100 and the connections with the metal strips are protected and covered with coatings 140, 141, and wires 101 extending from the metal strips are insulated. Likewise, conductors 221, 222 in sensors 200, 200', 300, 400, 400', 500, 600 and the connections with testing elements and resistors are covered and protected with layer 240 on base 110. In general, the connections (a) between the leads and the testing element, (b) between the leads and the reference element (if any), and (c) between the leads and the reference resistor (if any) may be formed by any suitable means such as soldering. In other embodiments, the testing circuit and reference circuit (if any) may be incorporated into a printed circuit board (PCB) with the conductors (e.g., conductors 121, 122, 131, 221, 222) being traces or printed wires. After soldering the connections to the leads, the PCB may then be potted in a non-conductive water-proof material such as epoxy.

In each of the embodiments previously described (e.g., sensors 100, 200, 200', 300, 400, 400', 500, 600), corrosion is detected by applying a voltage differential across a pair of conductors, measuring the current through the conductors, and then determining the resistance across the conductors. If the testing element has corroded, the determined resistance will increase. The determined resistance may be the actual resistance across the corroded element or the resistance of a reference resistor placed in parallel with the testing element. Although this technique is relatively simple, it does require an inspector physically connect a meter to the conductors at the location being inspected.

Figure 15:
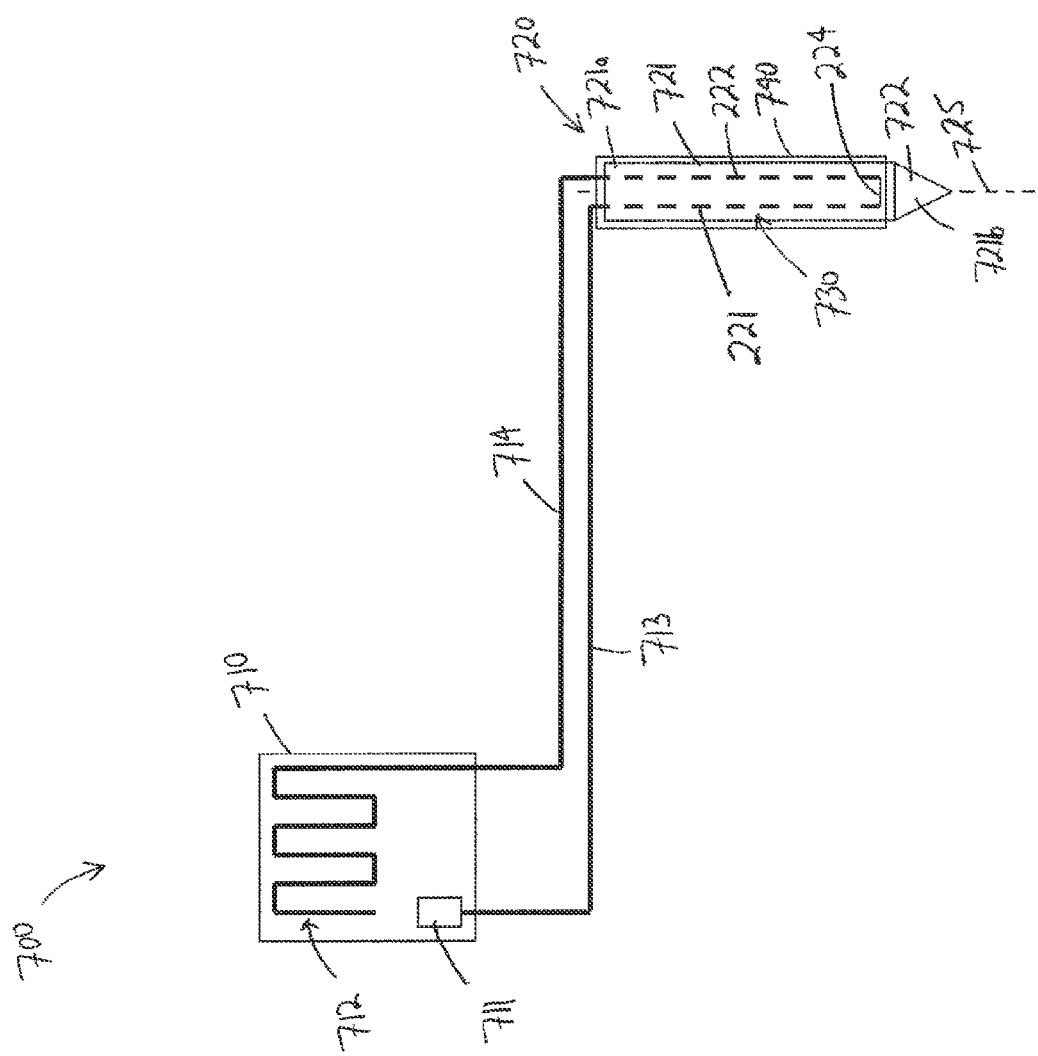
FIG. 15 is a front view of an embodiment of a CUI sensor in accordance with the principles described herein.

Referring now to FIG. 15, an embodiment of a wirelessly and remotely readable sensor 700 for detecting CUI is shown. In this embodiment, sensor 700 comprises a radio-frequency identification (RFID) tag 710 and a CUI testing member 720.

RFID tag 710 includes an integrated RFID circuit 711 and an antenna 712. Circuit 711 is coupled to antenna 712 through testing member 720. In other words, circuit 711 and antenna 712 communicate with each other through testing member 720.

Circuit 711 stores and processes information about itself or the object to which it is coupled (e.g., a tag identifier, a weld pack identifier, whether the weld pack is an original weld pack or rehabilitated weld pack, etc.), and modulates and demodulates a radio-frequency (RF) signal. Antenna 712 receives and transmits the RF signal carrying the information. The information stored in circuit 711 is acquired by an RFID reader carried by a user and scanned over or aimed at RFID tag 710. In this embodiment, RFID tag 710 is a passive RFID tag that includes no internal power source, and is only active (i.e., responds to the reader) when the reader is nearby.

Testing member 720 comprises a base 721 and a testing circuit 730 mounted to base 721. In this embodiment, base 721 is an elongate pin having a central or longitudinal axis 725, a first end 721a, and a second end 721b opposite first end 721a. Second end 721b comprises a conical surface 722 to facilitate advancement of testing member 720 into insulation (e.g., insulation 13, 16). Base 721 preferably comprise a rigid, non-conductive material such as fiberglass or plastic. In this embodiment, base 721 is a fiberglass pin having a diameter of 0.25 in. In other embodiments, the base (e.g., base 721) is the same as base 110 previously described.

Figure 16:
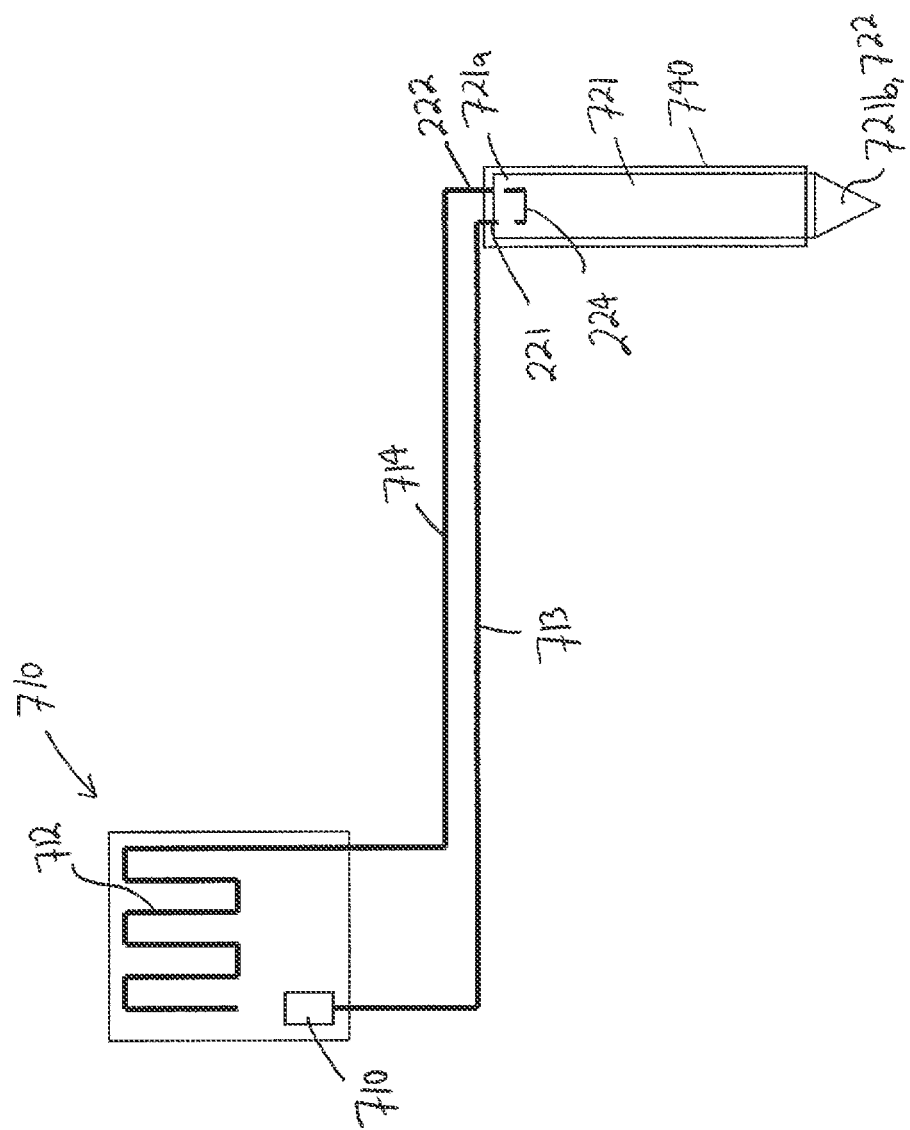
FIG. 16 is a front view of an embodiment of a CUI sensor in accordance with the principles described herein.

Testing circuit 730 is mounted to base 721 and includes a pair of test conductors 221, 222 and a test or testing element 224 extending between conductors 221, 222, each as previously described. Conductors 221, 222 and element 224 are each as previously described. In this embodiment, testing element 224 is positioned axially adjacent end 721b, however, as shown in FIG. 16, element 224 may be positioned proximal end 721a. Conductors 221, 222 extend axially along base 721 and are covered with a non-conductive water-proof layer or coating 740 such as a fiberglass laminate, however, testing element 224 is disposed outside coating 740. In other words, testing element 224 is completely exposed to the environment around testing member 720. Circuit 711 is not directly connected to antenna 712. Rather, circuit 711 is coupled to conductor 221 with a wire 713, and antenna 712 is coupled to conductor 222 with a wire 714. Thus, communications between circuit 711 and antenna 712 pass through element 224.

Figure 17:
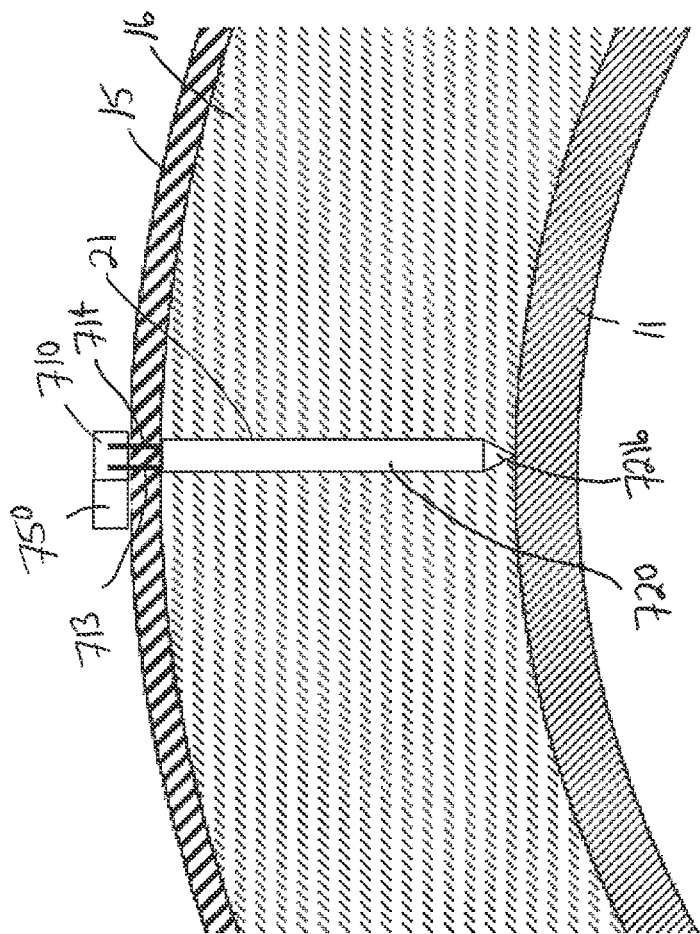
FIG. 17 is a cross-sectional end view of the weld pack of FIGS. 1 and 2 with the CUI sensor of FIG. 15 installed.
Figure 18:
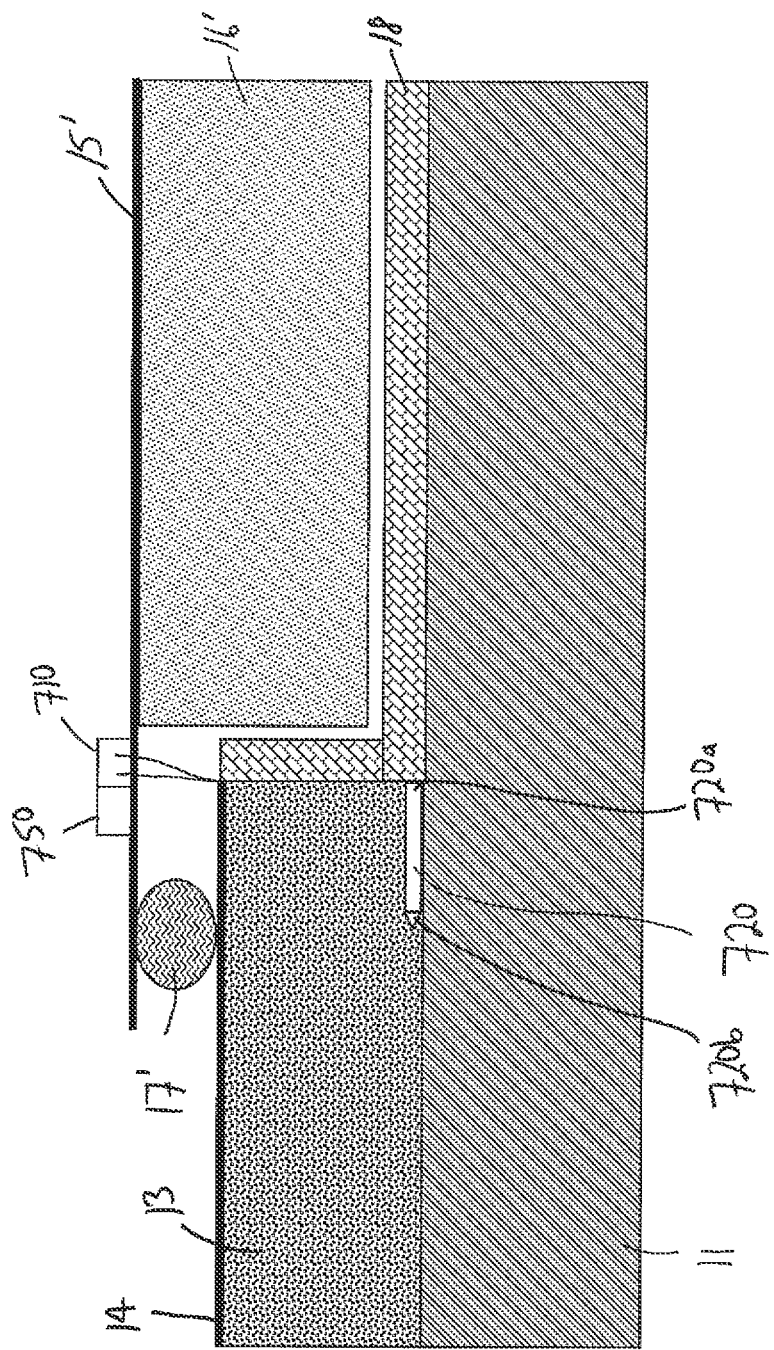
FIG. 18 is a cross-sectional end view of the weld pack of FIG. 3 with the CUI sensor of FIG. 16 installed.

As shown in FIG. 17, with element 224 positioned axially adjacent end 721b, testing member 720 is installed in the same manner as sensor 200 (with element 224 directly contacting insulation 16 radially adjacent pipe segment 11) to detect corrosion of pipe segment 11 beneath insulation 16. However, as shown in FIG. 18, with element 224 positioned axially adjacent end 721a, testing member 720 is installed in the same manner as sensor 200' (with element 224 directly contacting insulation 16 radially adjacent pipe segment 11 and axially adjacent barrier 18) to detect corrosion of pipe segment 11 beneath insulation 13. In embodiments where jacket 15, 15' is metal, RFID tag 710 is preferably positioned external weld pack 20, 20', respectively, with wires 713, 714 routed through seal 17 or through jacket 15 to conductors 221, 222. A seal is preferably formed around each wire 713, 714 to restrict and/or prevent moisture from passing through seal 17 or jacket 15. However, in embodiments where jacket 15, 15' is a non-metal (e.g., plastic), RFID tag 710 may be positioned inside weld pack 20, 20', respectively.

To assess whether element 224 has corroded, indicating pipe segment 11 may have corroded, the reader is pass over or aimed at RFID tag 710. If element 224 is intact, RFID tag 710 will respond to the reader, however, if element 224 is corroded through, then circuit 711 cannot communicate with antenna 712 and RFID tag 710 will not respond to the reader. Therefore, by simply passing the reader across RFID tag 710, inspectors can easily assess whether element 224 is corroded, thereby enhancing the speed and ease with which corrosion of element 224 may be identified.

RFID tag 710 may be positioned in radial alignment with testing member 720 so that location of RFID tag 710 may be used to identify the location of element 224. However, a second, conventional RFID tag 750 is preferably positioned immediately adjacent RFID tag 710 to allow automatic recording of corrosion data and location regardless of the state of RFID tag 710. For example, if element 224 has corroded through, RFID tag 710 will not communicate any information to the reader, and thus, second RFID tag 750 may be relied upon to (a) confirm the reader is working correctly and is properly positioned, and (b) to communicate the location of RFID tag 710, which is associated with the corrosion data (i.e., that RFID tag 710 did not respond, and thus, corrosion is detected).

Embodiments of CUI sensors 100, 200, 200', 300, 300', 400, 500, 700 described above enable a relatively quick, non-invasive identification of whether corrosion is or is not occurring at or near the location of the sensor. In general, CUI sensors 100, 200, 200', 300, 300', 400, 500, 700 provide an indication that corrosion has occurred at or near the location of the sensor, and in some cases (e.g., sensors 100, 500), may provide an estimate of the degree of corrosion and/or corrosion rate. Once corrosion is detected, however, a subsequent inspection such as a TRT inspection or visual inspection is preferably performed to better locate, examine, and assess the actual corrosion on the underlying pipe segment(s). On the other hand, if no corrosion is detected, the inspectors can promptly move on and inspect another weld pack or CUI susceptible area of the pipeline.

In the embodiments described above, a single sensor (e.g., sensor 100, 200, 200', 300, 400, 400', 500, 600, 700) is employed to function as a proxy for the underlying carbon steel pipe segment (e.g., pipe segment 11). Thus, such embodiments are adapted to detect corrosion at a single location—the location where the sensor is positioned. However, in some applications, it may be desirable to (a) detect corrosion at more than one location, (b) identify the particular location(s) on the pipe segment where corrosion has occurred, (c) understand the corrosion rate (e.g., mils per year), or combinations thereof. From experience, it is known that the area on a pipe segment 11 within an original weld pack 20 most likely to get wet and start corroding first is the very bottom of the pipe segment (i.e., the 6:00 o'clock position) at the interface between the shop-applied insulation 13 and field-applied insulation 16, and the area on a pipe segment within a rehabilitated weld pack 20' most likely to get wet and start corroding first is the very bottom of the pipe segment at the interface between the shop-applied insulation 13 and barrier 18. However, it is also known from experience that these CUI susceptible areas may not always represent the location with the highest corrosion rate. For at least these reasons, it may be advantageous to employ CUI sensor arrays including multiple CUI sensors positioned at different axial and/or circumferential locations along the pipe segment being monitored. In general, any sensor embodiment disclosed herein (e.g., sensors 100, 200, 200', 300, 400, 400', 500, 600, 700) may be included in an array of sensors. Some exemplary arrays including sensors 200, 200', 300, 400, 400', 500, and 700 will now be described in greater detail.

Figure 19:
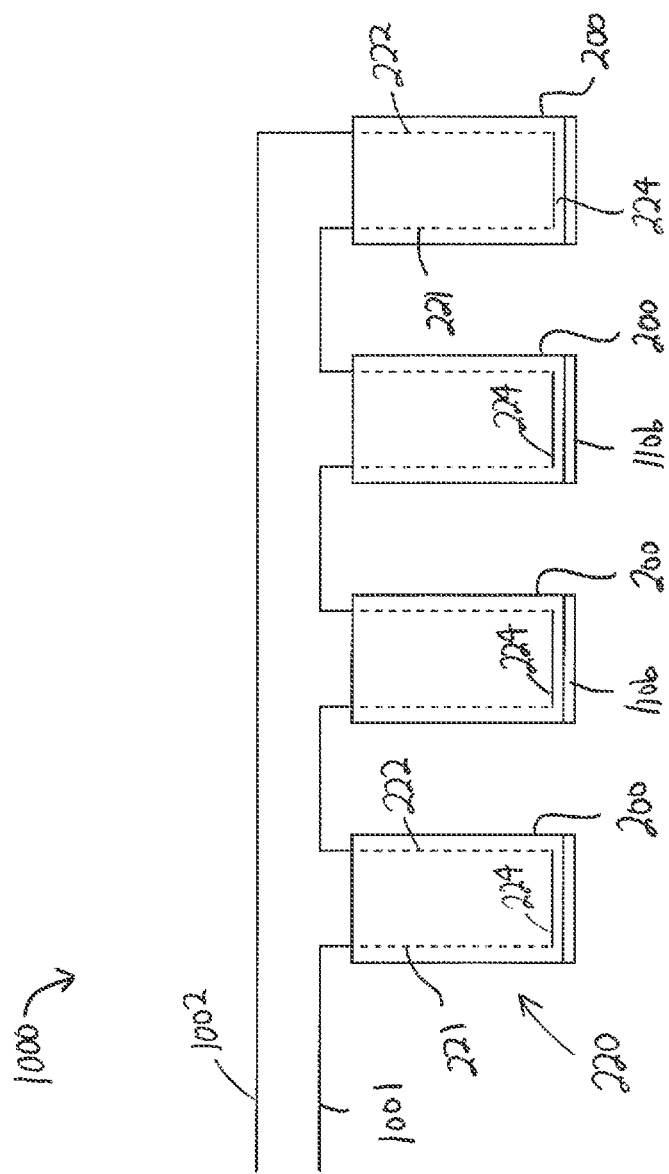
FIG. 19 is a front view of an embodiment of an array including a plurality of the CUI sensors of FIGS. 6a and 6b and in accordance with the principles described herein.

Referring now to FIG. 19, an embodiment of an array 1000 including a plurality of sensors 200 previously described is shown. Sensors 200 are connected in series between a pair of electrical conductors 1001, 1002. In this embodiment, conductors 1001, 1002 are insulated wires. Although four sensors 200 are shown in this embodiment, in general, any number of sensors (e.g., sensors 200) may be included in the array (e.g., array 1000). For most applications, array 1000 preferably includes four to eight sensors 200, although more may be desirable.

By applying a voltage differential across conductors 1001, 1002 and measuring the current flow through array 1000, the total resistance across all testing elements 224 is determined. As long as each element 224 is intact, the determined resistance between wires 1001, 1002 will be very low (~0 ohms). However, if any one or more of testing elements 224 have corroded through, it will create an open circuit between conductors 1001, 1002 and the determined resistance will be very high.

Figure 20:
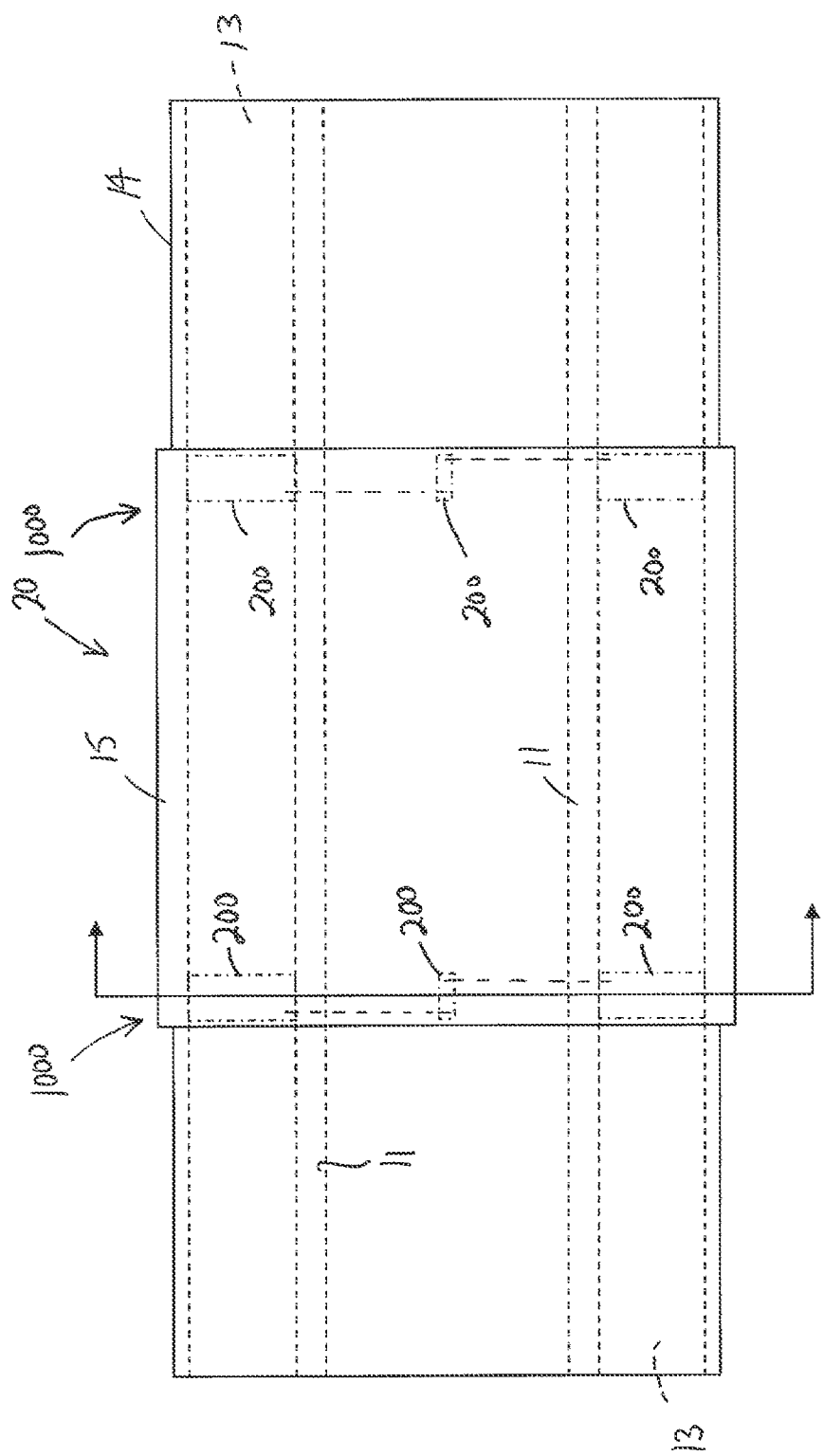
FIG. 20 is a side view of the weld pack of FIGS. 1 and 2 with the array of FIG. 19 installed.
Figure 21:
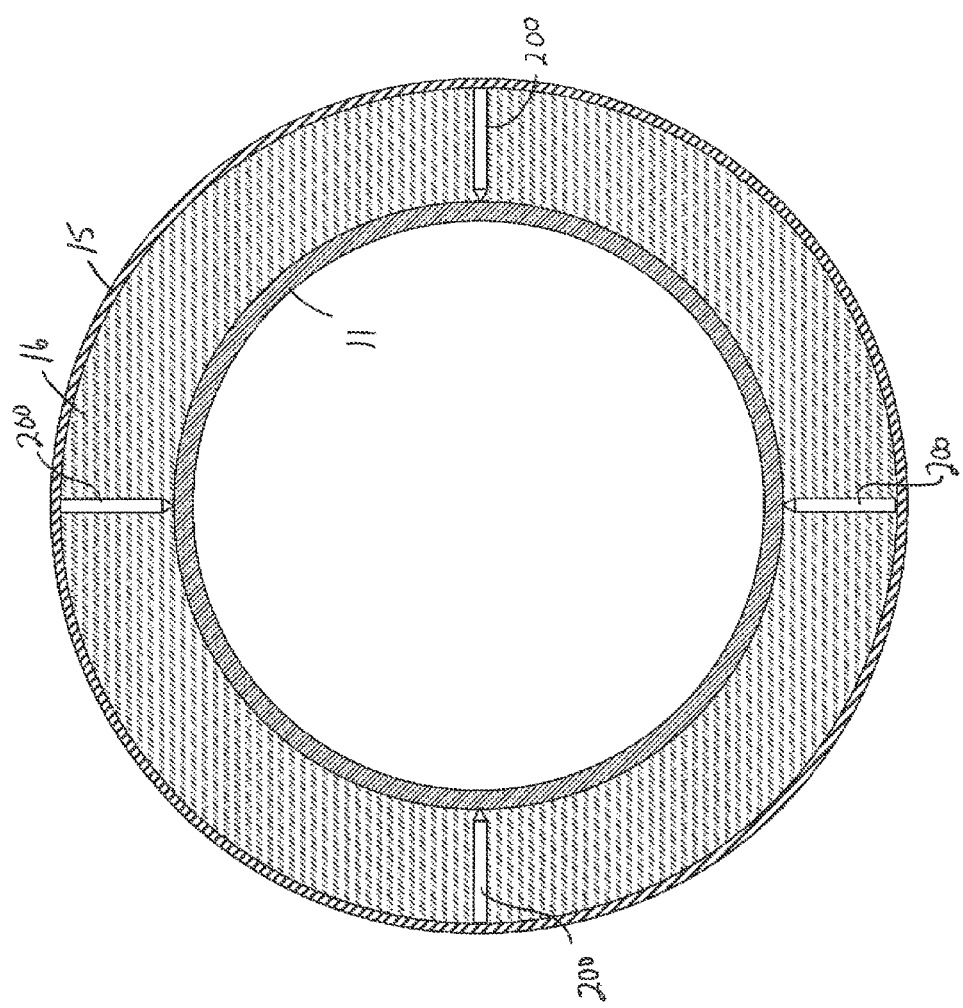
FIG. 21 is a cross-sectional end view of the weld pack and array of FIG. 20.

As discussed above, the lower portion of a pipe segment 11 at the interface between the shop-applied insulation 13 and field-applied insulation 16 in an original weld pack 20 is typically the area of the pipe segment 11 most likely to get wet and start corroding first. Accordingly, at least one sensor 200 is preferably positioned along the lower half of each pipe segment 11 at each interface between insulation 16 and the axially adjacent insulation 13 as shown in FIGS. 20 and 21. At a given weld pack 20, field-applied insulation 16 interfaces with shop-applied insulation 13 at two locations (at both ends of field-applied insulation 16). Thus, to detect corrosion at multiple locations along the two CUI susceptible areas of pipe segments 11, sensors 200 of a first array 1000 are circumferentially spaced about one pipe segment 11 axially adjacent one interface of insulation 13, 16 in weld pack 20, and sensors 200 of a second array 1000 are circumferentially-spaced about the other pipe segment 11 axially adjacent the other interface of insulation 13, 16 in weld pack 20. In this embodiment, sensors 200 of each array 1000 are uniformly circumferentially-spaced 90° apart with one sensor 200 disposed at bottom dead center of its corresponding pipe segment 11 (the 6 o'clock position) as this is a high-probability of corrosion location. In other words, sensors 200 of each array 1000 may be described as being disposed at the 3, 6, 9, and 12 o'clock positions.

Although sensors 200 of each array 1000 are described as being uniformly circumferentially-spaced about the entire circumference of an associated pipe segment 11, in other embodiments, sensors 200 of an array 1000 may be non-uniformly circumferentially-spaced, concentrated in a particular portion of the circumference of the associated pipe segment 11, or combinations thereof. For example, to specifically focus on corrosion along the lower half of a pipe segment 11, sensors 200 of an array 1000 may be concentrated along the lower half of one pipe segment 11 axially adjacent one interface of insulation 13, 16. In particular, at the interface of insulation 13, 16, one sensor 200 may be installed at bottom dead center (i.e., the 6 o'clock position), as this is a high-probability of corrosion location, and to further improve the probability of detection, the remaining two sensors 200 may be circumferentially-spaced 45° to either side of bottom dead center (i.e., at the 4:30 and 7:30 positions). The fourth sensor 200 of the array 1000 may be positioned at any other desired location such as at top dead center (the 12 o'clock position). Further, although one array 1000 is provided for each interface between insulation 13, 16 in a given weld pack 20, in other embodiments, a single array including a plurality of sensors 200 may be employed to simultaneously detect corrosion at both interfaces of insulation 13, 16 in a given weld pack 20. For example, a single array including eight sensors 200 may be deployed with four sensors 200 positioned at each interface of insulation 13, 16 in the manner previously described.

Referring still to FIGS. 19-21, to inspect each pipe segment 11 within original weld pack 20, a meter is employed to apply a voltage differential across conductors 1001, 1002 of each array 1000, measure the current in conductors 1001, 1002, and determine the total resistance across all testing elements 224 in that array 1000. If each element 224 is intact, the measured resistance between wires 1001, 1002 will be very low (~0 ohms), thereby indicating very little, if any, corrosion of the CUI susceptible areas of pipe segments 11 within weld pack 20. However, if any one or more of testing elements 224 have corroded through, the measured resistance between wires 1001, 1002 will be relatively high, thereby indicating corrosion of at least one CUI susceptible area of pipe segments 11. Since sensors 200 in each array 1000 are in series and a relatively high resistance will occur if any one or more elements 224 corrodes completely through, a relatively high resistance is only indicative of corrosion somewhere proximate one or more sensors 200. Thus, although this embodiment enables a relatively quick, non-invasive identification of whether corrosion is or is not occurring, it does not enable the inspector to determine which specific element 224 corroded through, the specific location of the corrosion, how many elements 224 corroded through, or whether the corrosion is occurring at multiple locations. Consequently, if no corrosion is detected with array 1000, the inspectors can promptly move on and inspect another array 1000, weld pack or CUI susceptible area of the pipeline. However, if corrosion is detected with an array 1000, a subsequent inspection such as a TRT inspection is preferably performed to better locate, examine, and assess the corrosion.

Figure 22:
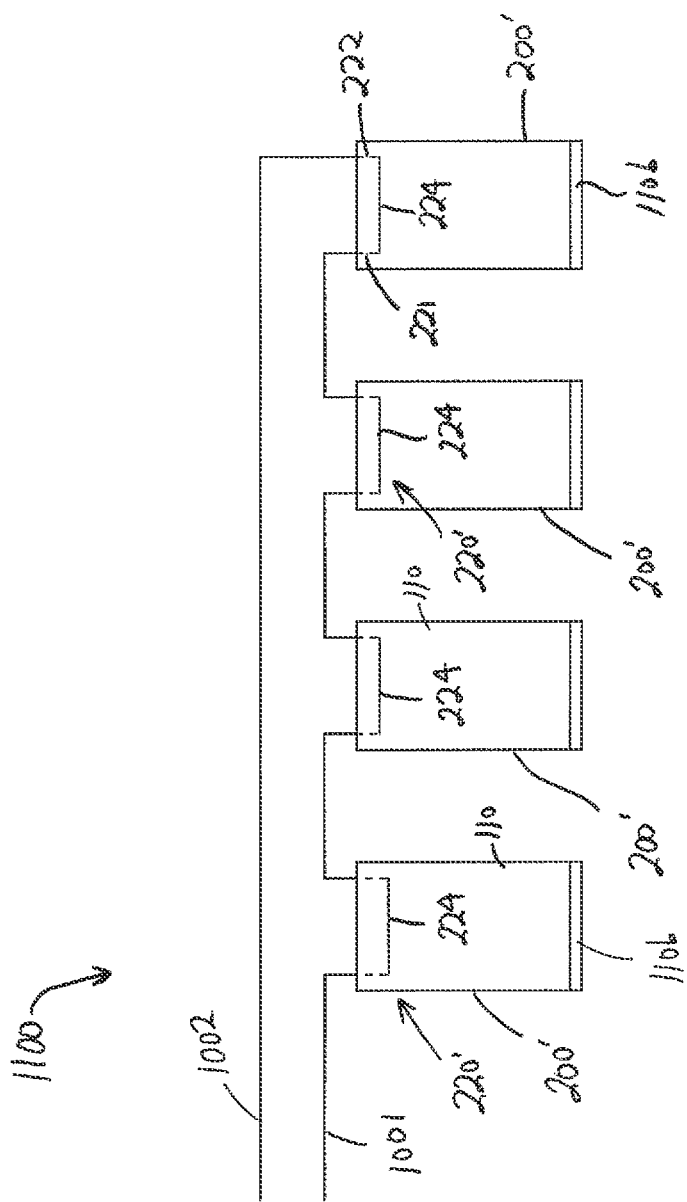
FIG. 22 is a front view of an embodiment of an array including a plurality of the CUI sensors of FIGS. 8a and 8b and in accordance with the principles described herein.

Referring now to FIG. 22, an embodiment of an array 1100 including a plurality of sensors 200' previously described is shown. Sensors 200' are connected in series between conductors 1001, 1002 previously described. Although four sensors 200' are shown in this embodiment, in general, any number of sensors (e.g., sensors 200') may be included in the array (e.g., array 1100). For most applications, array 1100 preferably includes four to eight sensors 200'.

By applying a voltage differential across conductors 1001, 1002 and measuring the current flow through array 1100, the total resistance across all testing elements 224 is determined. As long as each element 224 is intact, the determined resistance between wires 1001, 1002 will be very low (~0 ohms). However, if any one or more of testing elements 224 have corroded through, it will create an open circuit between conductors 1001, 1002 and the determined resistance will be very high.

Figure 23:
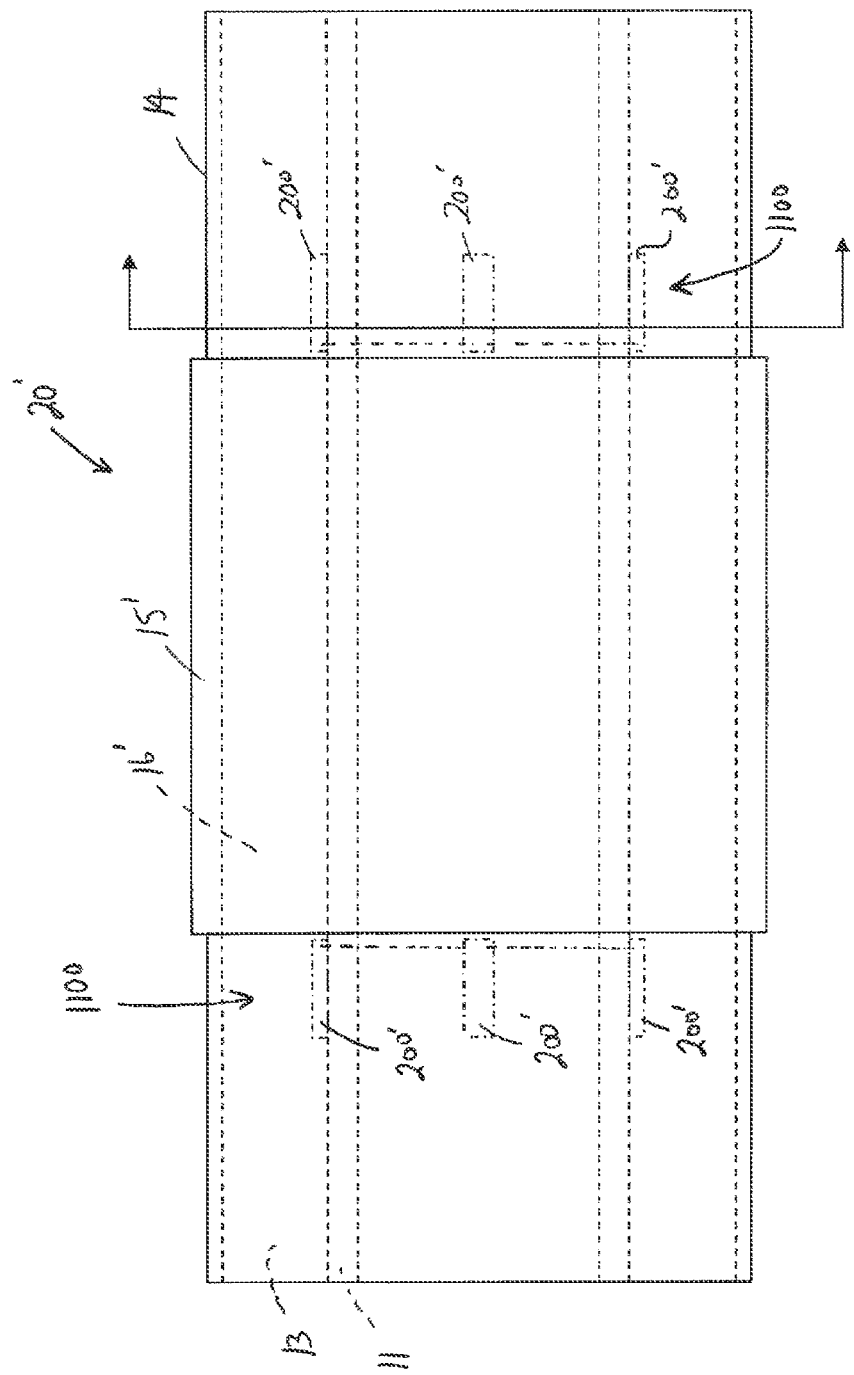
FIG. 23 is a side view of the weld pack of FIG. 3 with the array of FIG. 22 installed.
Figure 24:
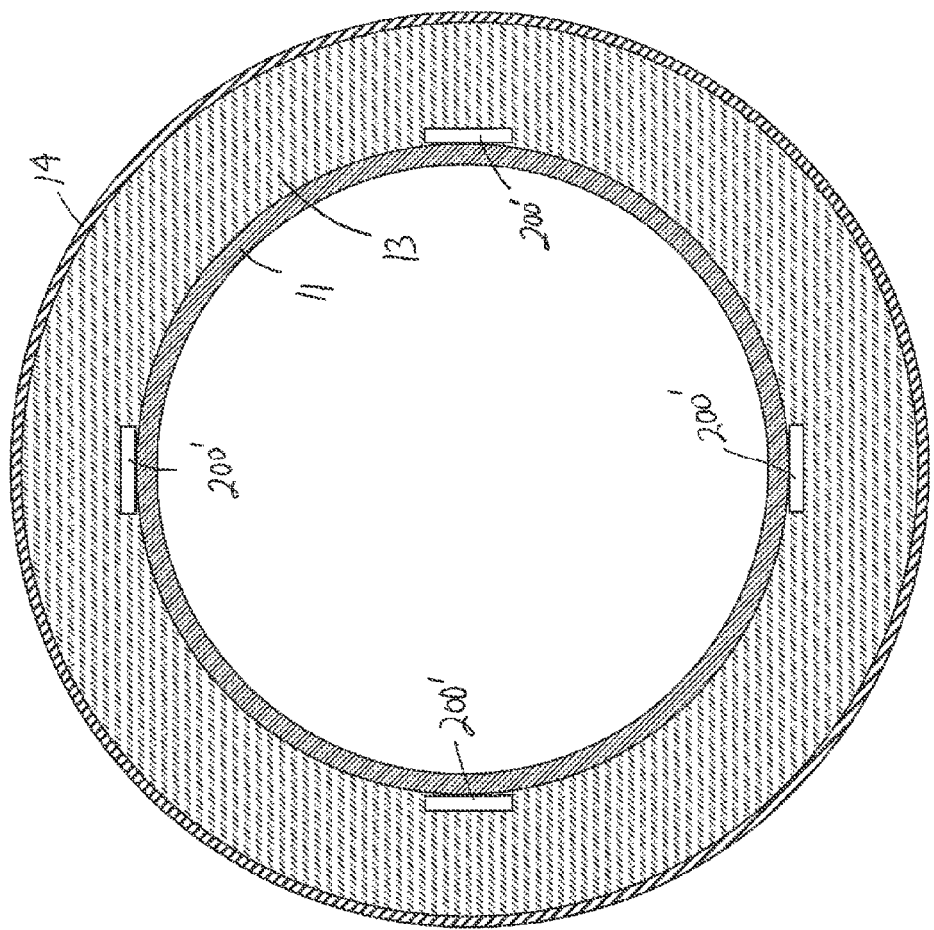
FIG. 24 is a cross-sectional end view of the weld pack and array of FIG. 23.

In this embodiment, array 1100 is used to detect corrosion in rehabilitated weld pack 20'. To simplify installation, sensors 200' of array 1100 are preferably installed as described below at the time rehabilitation is being performed. As discussed above, the lower portion of a pipe segment 11 at the interface between the shop-applied insulation 13 and barrier 18 in a rehabilitated weld pack 20' is typically the area of the pipe segment 11 most likely to get wet and start corroding first. Accordingly, at least one sensor 200' is preferably positioned along the lower half of each pipe segment 11 at each interface between insulation 13 and barrier 18 as shown in FIGS. 23 and 24. At a given weld pack 20', shop-applied insulation 13 interfaces with barrier 18 at two locations (at both end faces of insulation 13). Thus, to detect corrosion at multiple locations along the two CUI susceptible areas of pipe segments 11, sensors 200' of a first array 1100 are circumferentially-spaced about one pipe segment 11 axially adjacent one interface of insulation 13 and barrier 18 in weld pack 20', and sensors 200' of a second array 1100 are circumferentially-spaced about the other pipe segment 11 axially adjacent the other interface of insulation 13 and barrier 18 in weld pack 20'. In this embodiment, sensors 200' of each array 1100 are uniformly circumferentially-spaced 90° apart with one sensor 200' disposed at bottom dead center of its corresponding pipe segment 11 (the 6 o'clock position) as this is a high-probability of corrosion location. In other words, sensors 200' of each array 1100 are disposed at the 3, 6, 9, and 12 o'clock positions.

Although sensors 200' of each array 1100 are described as being uniformly circumferentially-spaced about the entire circumference of an associated pipe segment 11, in other embodiments, sensors 200' of an array 1100 may be non-uniformly circumferentially-spaced, concentrated in a particular portion of the circumference of the associated pipe segment 11, or combinations thereof. For example, to specifically focus on corrosion along the lower half of a pipe segment 11, sensors 200' of an array 1000 may be concentrated along the lower half of one pipe segment 11 axially adjacent one interface of insulation 13 and barrier 18. In particular, at the interface of insulation 13 and barrier 18, one sensor 200' may be installed at bottom dead center (i.e., the 6 o'clock position), as this is a high-probability of corrosion location, and to further improve the probability of detection, the remaining two sensors 200' may be circumferentially-spaced 45° to either side of bottom dead center (i.e., at the 4:30 and 7:30 positions). The fourth sensor 200' of the array 1100 may be positioned at any other desired location such as at top dead center (the 12 o'clock position). Further, although one array 1100 is provided for each interface between insulation 13 and barrier 18 in a given weld pack 20', in other embodiments, a single array including a plurality of sensors 200' may be employed to simultaneously detect corrosion at both interfaces of insulation 13 and barrier 18 in a given weld pack 20'. For example, a single array including eight sensors 200' may be deployed with four sensors 200' positioned at each interface of insulation 13 and barrier 18 in the manner previously described.

Referring still to FIGS. 22-24, array 1100 is operated in the same manner as array 1000 previously described to inspect pipe segments 11 within rehabilitated weld pack 20' (i.e., the resistance between wires 1001, 1002 is determined to assess corrosion of elements 224). Likewise, although this embodiment enables a relatively quick, non-invasive identification of whether corrosion is or is not occurring, it does not enable the inspector to determine which specific element 224 corroded through, the specific location of the corrosion, how many elements 224 corroded through, or whether the corrosion is occurring at multiple locations. Consequently, if no corrosion is detected with array 1100, the inspectors can promptly move on and inspect another weld pack or CUI susceptible area of the pipeline. However, if corrosion is detected with array 1100, a subsequent inspection such as a TRT inspection is preferably performed to better locate, examine, and assess the corrosion.

Figure 25:
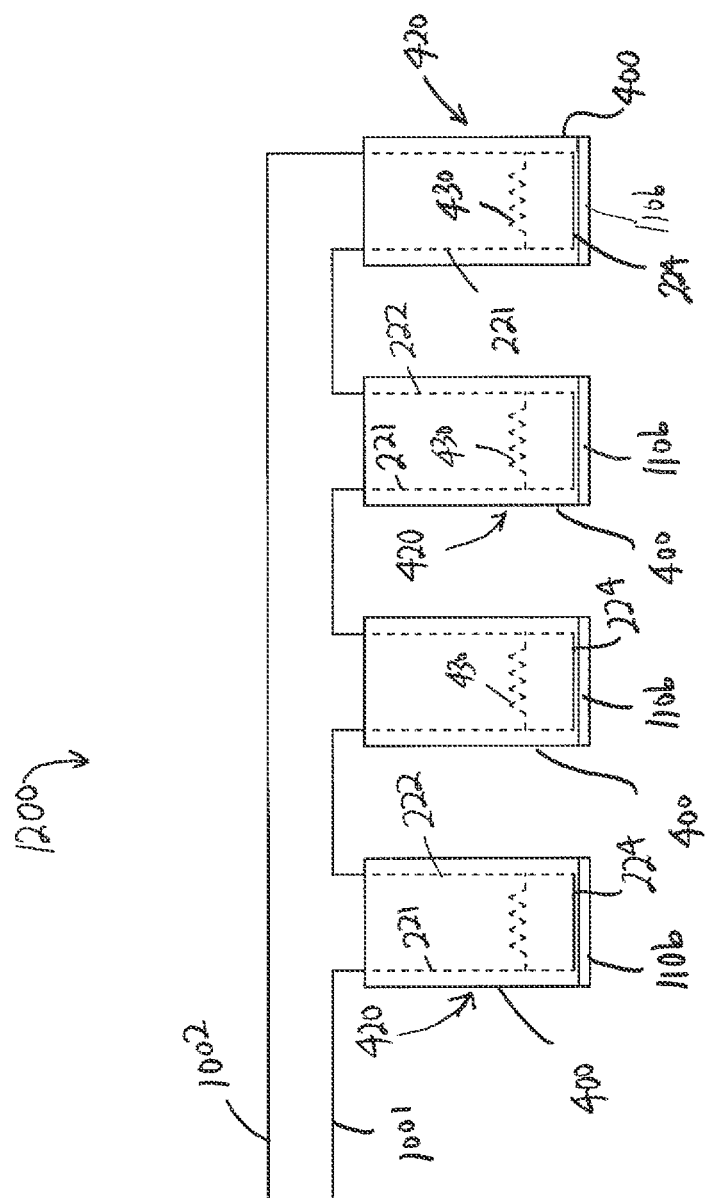
FIG. 25 is a front view of an embodiment of an array including a plurality of the CUI sensors of FIG. 11 and in accordance with the principles described herein.

Referring now to FIG. 25, an embodiment of an array 1200 including a plurality of sensors 400 previously described is shown. Sensors 400 are connected in series between conductors 1001, 1002 previously described. Although four sensors 400 are shown in this embodiment, in general, any number of sensors (e.g., sensors 300) may be included in the array (e.g., array 1200). For most applications, array 1200 preferably includes four to eight sensors 400.

By applying a voltage differential across conductors 1001, 1002 and measuring the current flow through array 1200, the total resistance across each sensor 400 is determined. As long as each element 224 is intact, the determined resistance between wires 1001, 1002 will be very low (~0 ohms). However, if any testing element 224 has corroded through, the resistance of its corresponding resistor 430 will be included in the determined resistance between wires 1001, 1002. For example, assuming each resistor 430 has a resistance of 10 ohms, if one element 224 corrodes through, the determined resistance will be about 10 ohms; if two elements 224 corrode through, the determined resistance will be about 20 ohms; if three elements 224 corrode through, the determined resistance will be about 30 ohms, and so on.

As previously described, elements 224 in sensors 400 are positioned adjacent ends 110b for detecting corrosion of pipe segments 11 in an original weld pack 20. Accordingly, as shown in FIGS. 26 and 27, sensors 400 are preferably distributed and positioned in the same manner as sensors 200 of array 1000 previously described.

Figure 26:
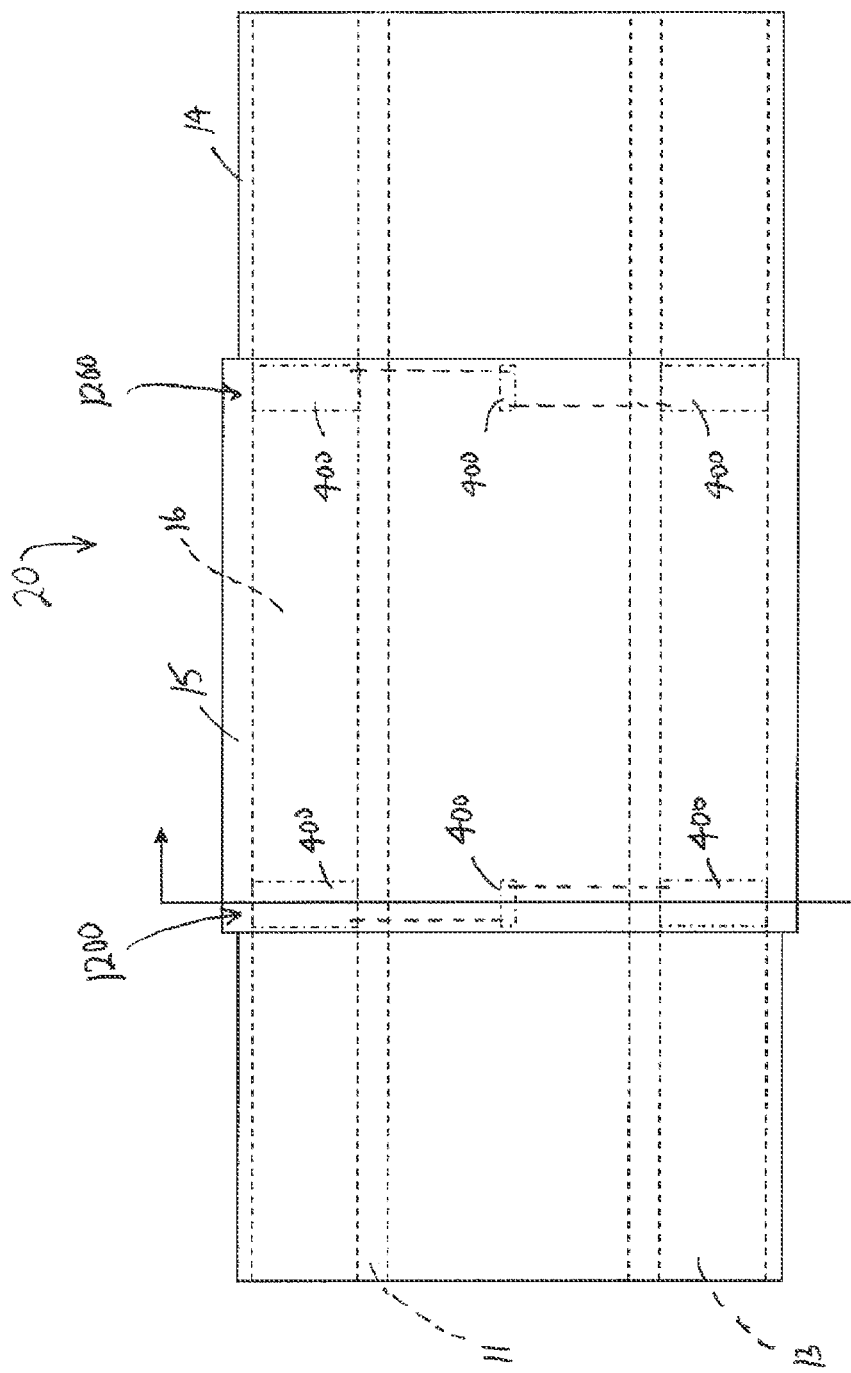
FIG. 26 is a side view of the weld pack of FIGS. 1 and 2 with the array of FIG. 25 installed.
Figure 27:
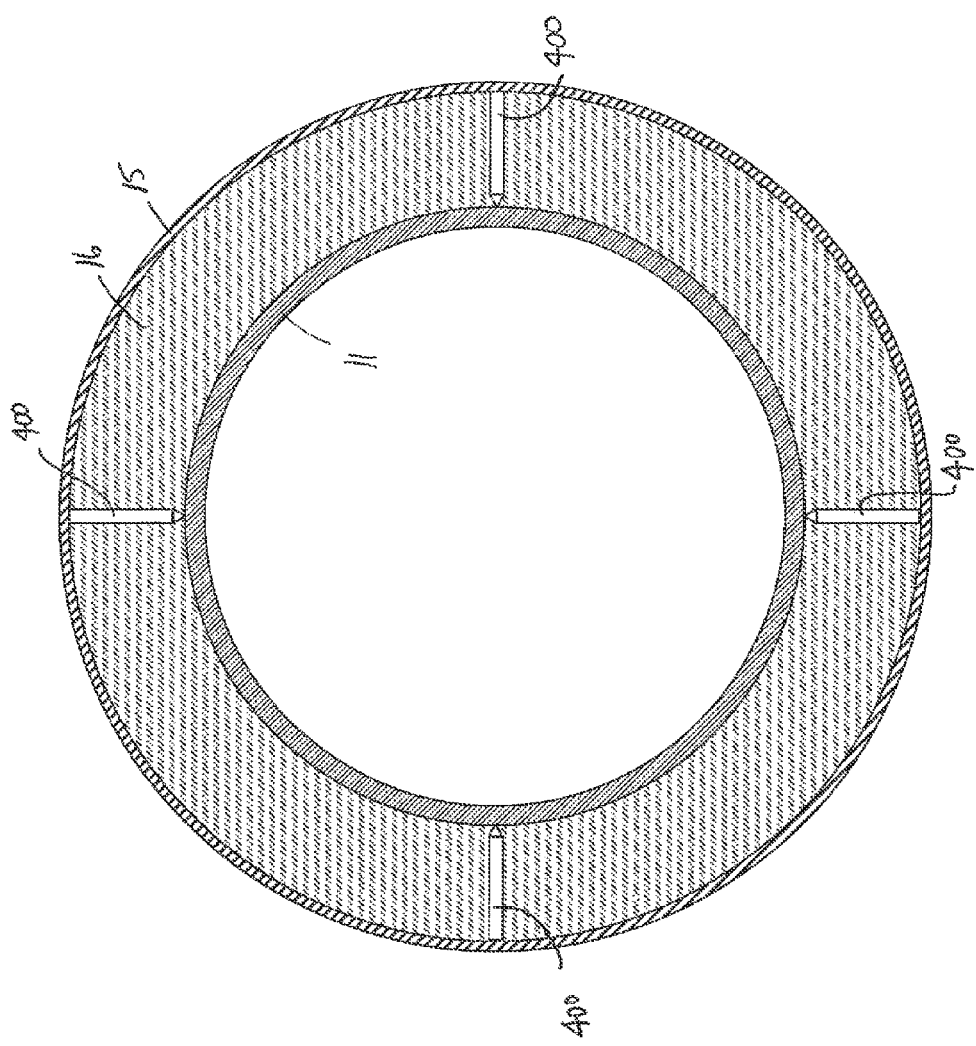
FIG. 27 is a cross-sectional end view of the weld pack and array of FIG. 26.

Referring still to FIGS. 25-27, once installed, each array 1200 is operated in the same manner as array 1000 to detect corrosion in pipe segments 11. In particular, to inspect pipe segments 11 within original weld pack 20, a meter is employed to apply a voltage differential across conductors 1001, 1002 of each array 1200, measure the current in conductors 1001, 1002, and determine the total resistance across all sensors 400 in that array 1200. If each element 224 is intact, the measured resistance between wires 1001, 1002 will be very low (~0 ohms), thereby indicating very little, if any, corrosion of the CUI susceptible areas of pipe segments 11 within weld pack 20. However, if any one or more of testing elements 224 have corroded through, the measured resistance between wires 1001, 1002 will be about the same as the sum of the resistances of the resistors 430 associated with each element 224 that has corroded through, thereby indicating corrosion of one or more CUI susceptible areas of pipe segments 11. If each resistor 430 has a known resistance, the number of elements 224 that have corroded can be calculated. For example, if each resistor 430 in an array 1200 has a resistance of 10 ohms and the resistance across all sensors 224 in that array 1200 is ~40 ohms, then all four elements 224 have corroded through, thereby indicating that four CUI susceptible areas of pipe segments 11 have corroded.

By employing resistors 430 with different, known resistances in array 1200, knowing the resistance of resistor 430 in each sensor 400, and knowing the position of each sensor 400 the particular sensors 300 having corroded elements 224, and hence the CUI susceptible areas on pipe segments 11 at which corrosion has occurred, may be determined. For instance, in an exemplary embodiment of array 120, a resistor 430 of a first sensor 400 has a resistance of 25 ohms, a resistor 430 of a second sensor 400 has a resistance of 50 ohms, a resistor 430 of a third sensor 400 has a resistance of 100 ohms, and a resistor 430 of a fourth sensor 400 has a resistance of 200 ohms; and it is known (e.g., based on the initial installation of sensors 400), that the first sensor 400 is positioned at the 3 o'clock position of the left insulation 13, 16 interface in FIG. 26, the second sensor 400 is positioned at the 6 o'clock position of the left insulation 13, 16 interface in FIG. 26, the third sensor 400 is positioned at the 9 o'clock position of the left insulation 13, 16 interface in FIG. 26, and the fourth sensor 400 is positioned at the 12 o'clock position of the left insulation 13, 16 interface in FIG. 26; then a determined resistance across all sensors 400 in that array 1200 is ~25 ohms, then element 224 of the first sensor 400 at the 3 o'clock position of the left insulation 13, 16 interface in FIG. 26 has corroded through, indicating corrosion along the left pipe segment 11 at or near that location; and if the determined resistance across all sensors 40 in that array 1200 is ~75 ohms, then element 224 of the first sensor 400 at the 3 o'clock position of the left insulation 13, 16 interface in FIG. 26 has corroded through and element 224 of the second sensor 400 at the 6 o'clock position of the left insulation 13, 16 interface in FIG. 26 has corroded through, indicating corrosion at or near these locations on pipe segments 11. To ensure the corrosion of different sets of two or more elements 224 in a given array 1200 cannot yield the same total determined resistance, the resistances of the resistors 430 in that array 1200 may be arranged such that each subsequent resistor 430 in the array 1200 has twice the resistance of the previous resistor 430 in the array 1200.

If no corrosion is detected with an array 1200, the inspectors can promptly move on and inspect another array 1200, weld pack or CUI susceptible area of the pipeline. However, if corrosion is detected with an array 1200, a subsequent inspection of the corroded area such as a TRT inspection is preferably performed to better locate, examine, and assess the corrosion.

Figure 28:
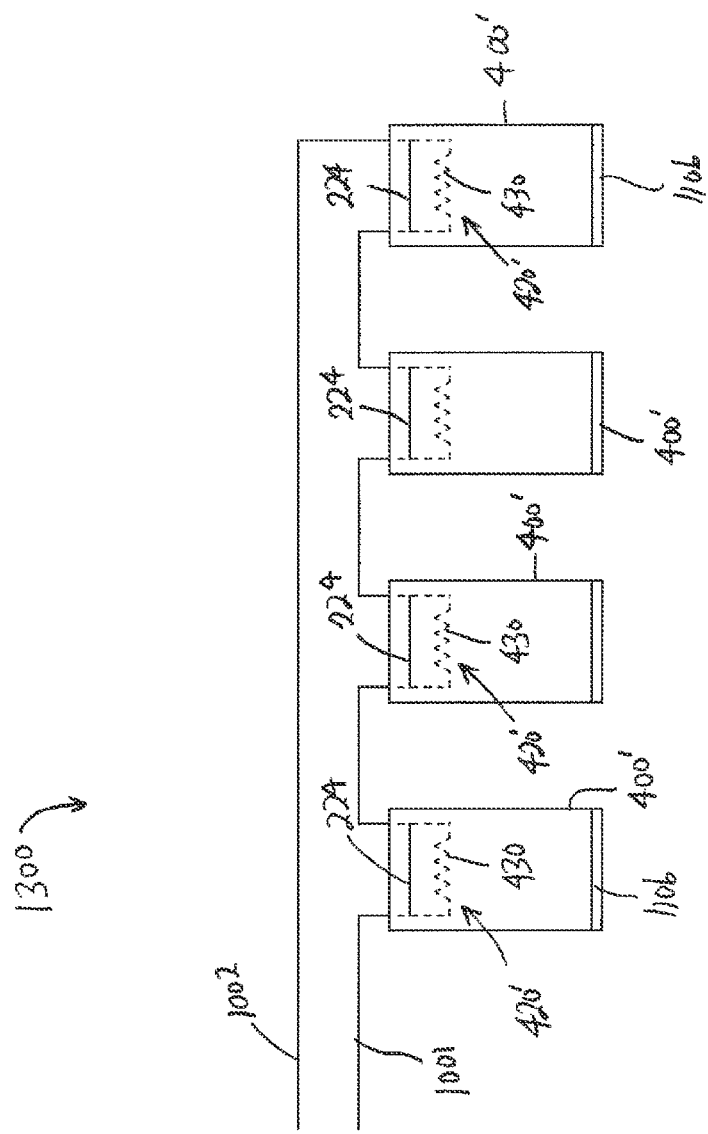
FIG. 28 is a front view of an embodiment of an array including a plurality of the CUI sensors of FIG. 12 and in accordance with the principles described herein.

Referring now to FIG. 28, an embodiment of an array 1300 including a plurality of sensors 400' previously described is shown. Sensors 400' are connected in series between conductors 1001, 1002 previously described. Although four sensors 400' are shown in this embodiment, in general, any number of sensors (e.g., sensors 400') may be included in the array (e.g., array 1300). For most applications, array 1300 preferably includes four to eight sensors 400'.

By applying a voltage differential across conductors 1001, 1002 and measuring the current flow through array 1300, the total resistance across each sensor 400' is determined. As long as each element 224 is intact, the determined resistance between wires 1001, 1002 will be very low (~0 ohms). However, if any testing element 224 has corroded through, the resistance of its corresponding resistor 430 will be included in the determined resistance between wires 1001, 1002. For example, assuming each resistor 430 has a resistance of 10 ohms, if one element 224 corrodes through, the determined resistance will be about 10 ohms; if two elements 224 corrode through, the determined resistance will be about 20 ohms; if three elements 224 corrode through, the determined resistance will be about 30 ohms, and so on.

Figure 29:
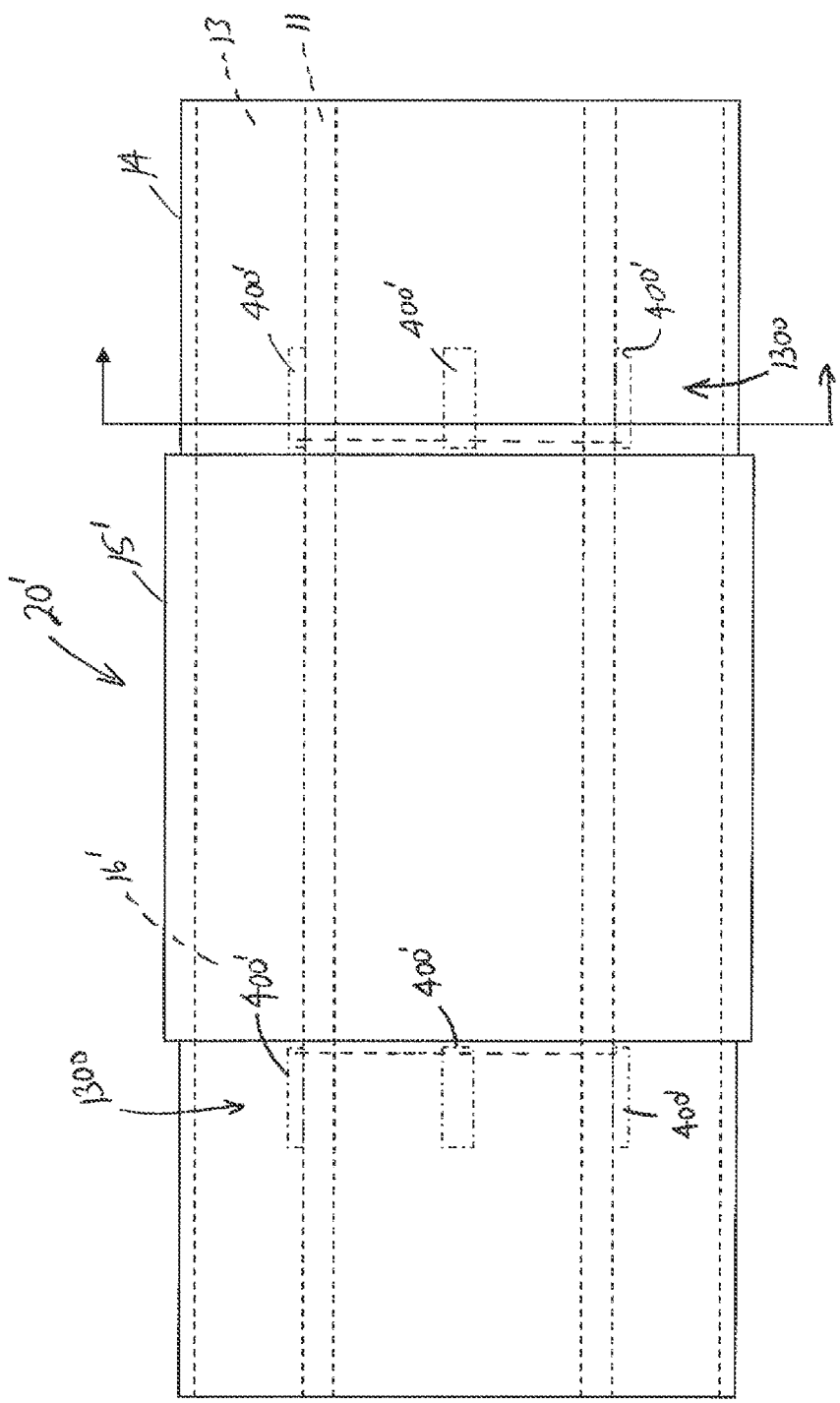
FIG. 29 is a side view of the weld pack of FIG. 3 with the array of FIG. 28 installed.
Figure 30:
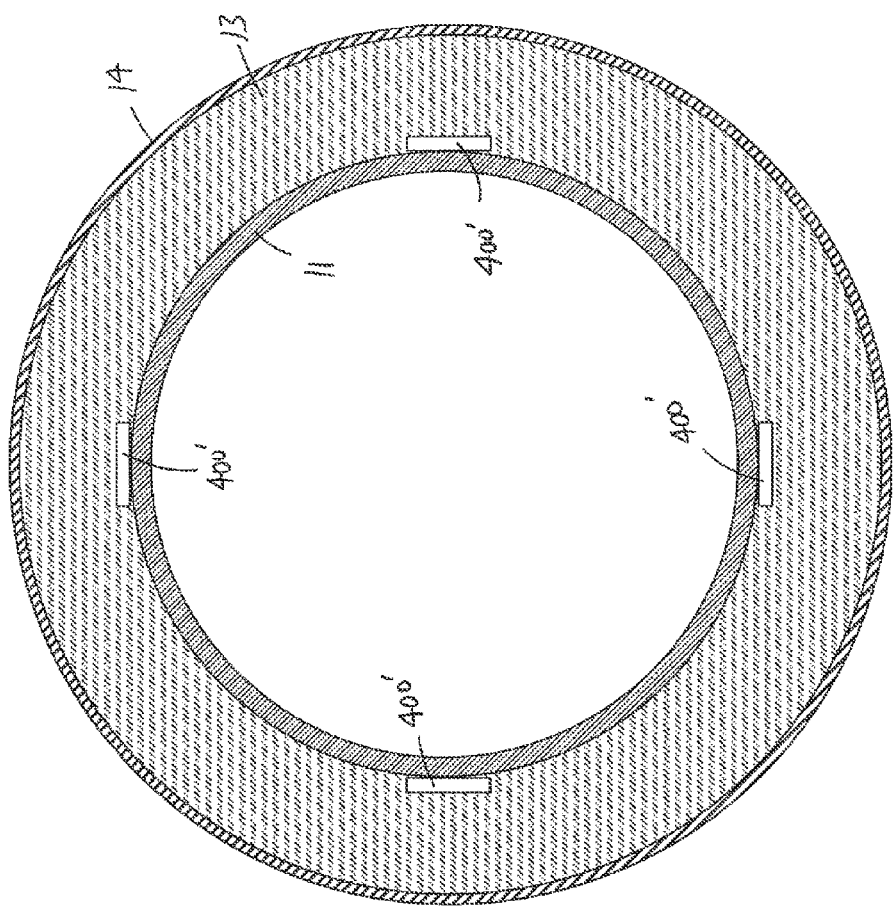
FIG. 30 is a cross-sectional end view of the weld pack and array of FIG. 29.

In this embodiment, array 1300 is used to detect corrosion in rehabilitated weld pack 20'. Accordingly, as shown in FIGS. 29 and 30, sensors 400' are preferably distributed and positioned in the same manner as sensors 200' of array 1100 previously described. To simplify installation, sensors 400' of array 1100 are preferably installed as described below at the time rehabilitation is being performed.

Referring still to FIGS. 28-30, array 1300 is operated in the same manner as array 1200 previously described to inspect pipe segments 11 within rehabilitated weld pack 20' (i.e., the resistance between wires 1001, 1002 is determined to assess corrosion of elements 224) and to identify the location of the corrosion. If no corrosion is detected with array 1300, the inspectors can promptly move on and inspect another array 1300, weld pack or CUI susceptible area of the pipeline. However, if corrosion is detected with array 1300, a subsequent inspection of the corroded area such as a TRT inspection is preferably performed to better locate, examine, and assess the corrosion.

Figure 31:
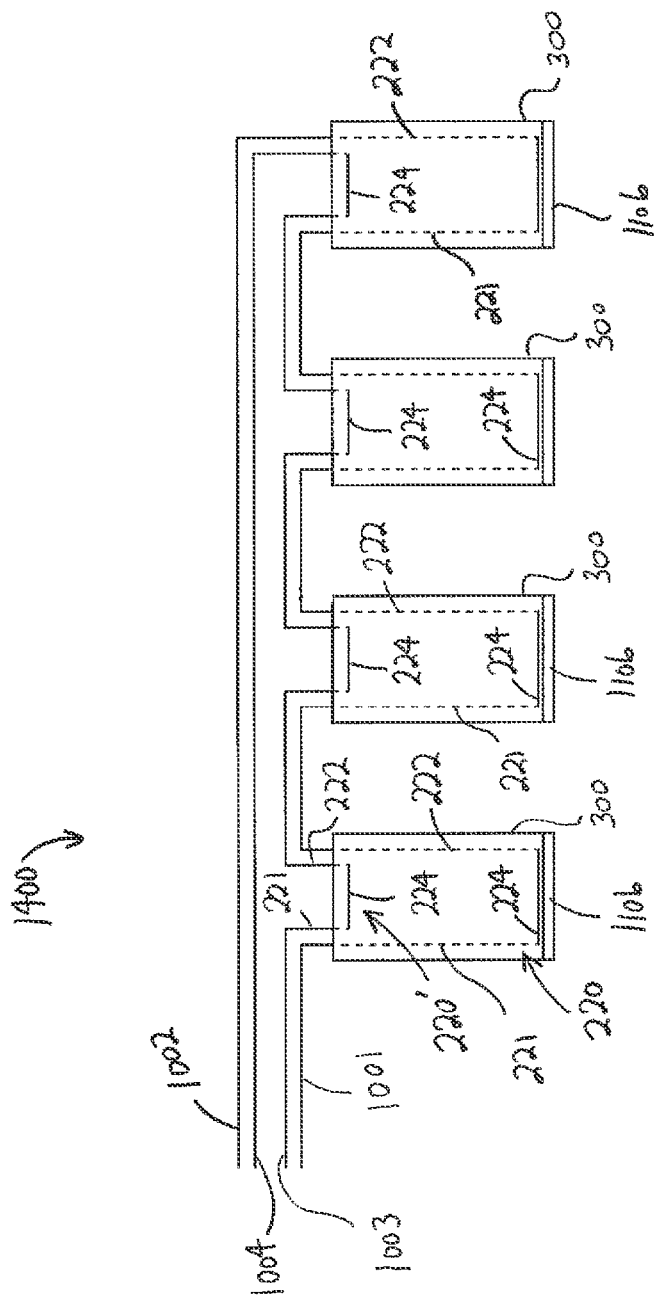
FIG. 31 is a front view of an embodiment of an array including a plurality of the CUI sensors of FIG. 10 and in accordance with the principles described herein.

Referring now to FIG. 31, an embodiment of an array 1400 including a plurality of sensors 300 previously described is shown. Testing circuits 220 are connected in series between a pair of electrical conductors 1001, 1002, and testing circuits 220' are connected in series between a pair of electrical conductors 1003, 1004. In this embodiment, conductors 1001, 1002, 1003, 1004 are insulated wires. Although four sensors 300 are shown in this embodiment, in general, any number of sensors (e.g., sensors 300) may be included in the array (e.g., array 1400). For most applications, array 1400 preferably includes four to eight sensors 300, although more may be desirable.

By applying a voltage differential across conductors 1001, 1002 and measuring the current flow therethrough, the total resistance across all testing circuits 220 is determined. As long as elements 224 in circuits 220 are intact, the determined resistance between wires 1001, 1002 will be very low (~0 ohms). However, if any one or more of testing elements 224 in circuits 220 have corroded through, it will create an open circuit between conductors 1001, 1002 and the determined resistance will be very high. Likewise, by applying a voltage differential across conductors 1003, 1004 and measuring the current flow therethrough, the total resistance across all circuits 220' is determined. As long as elements 224 in circuits 220' are intact, the determined resistance between wires 1003, 1004 will be very low (~0 ohms). However, if any one or more of testing elements 224 in circuits 220' have corroded through, it will create an open circuit between conductors 1003, 1004 and the determined resistance will be very high.

Since each sensor 300 includes an element 224 at each end 110a, b, array 1400 may be installed and operated in the same manner as array 1000 or array 1100 previously described. In other words, array 1400 may be employed to detect corrosion in an original weld pack 20 (i.e., at an interface between insulation 16 and the axially adjacent insulation 13) or in a rehabilitated weld pack 20' (i.e., at an interface between insulation 13 and barrier 18).

Using array 1400, an inspector can interrogate all circuits 220 with one resistance determination, and interrogate all circuits 220' with one resistance determination. The resistance across all circuits 220 provides the inspector with information about whether an element 224 in one or more of circuits 220 has corroded through, and the resistance across all circuits 220' provides the inspector with information about whether an element 224 in one or more circuits 220' has corroded through. However, the resistances do not indicate how many elements 224 have corroded through, or which specific elements 224 have corroded through.

Figure 32:
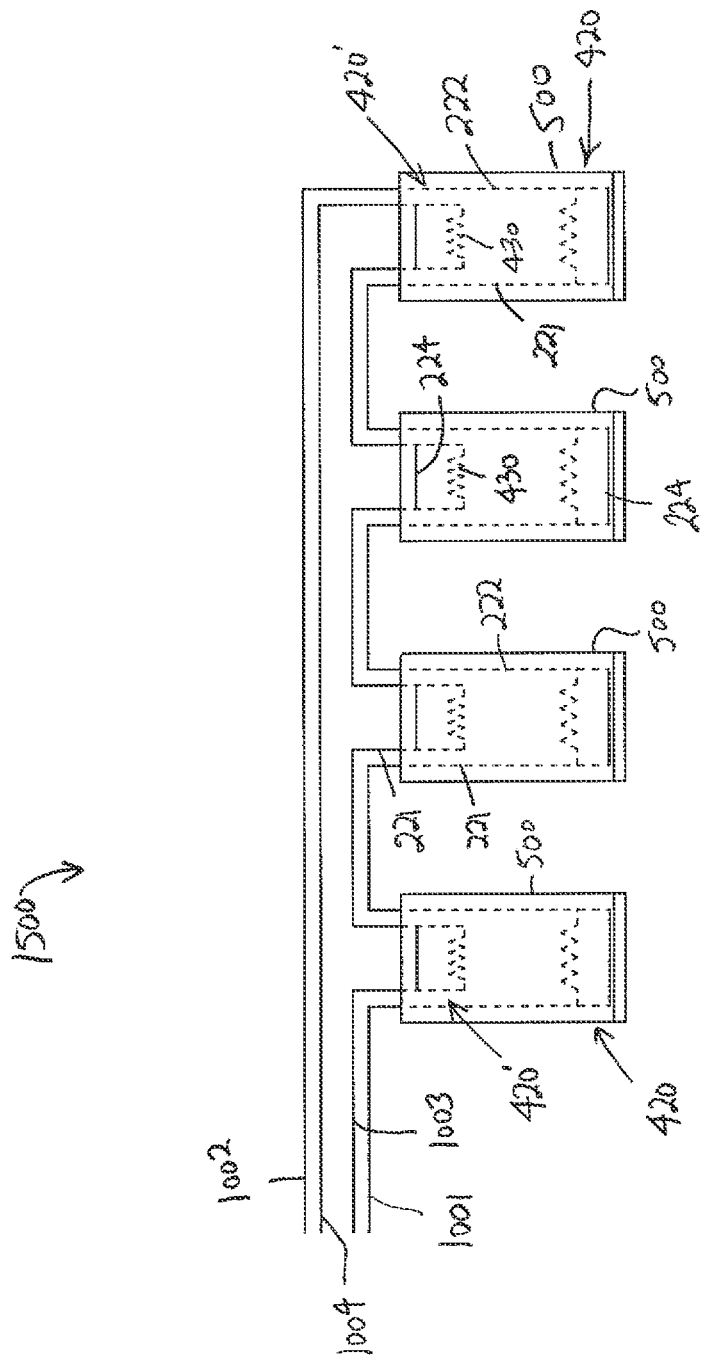
FIG. 32 is a front view of an embodiment of an array including a plurality of the CUI sensors of FIG. 13 and in accordance with the principles described herein.

Referring now to FIG. 32, an embodiment of an array 1500 including a plurality of sensors 500 previously described is shown. Testing circuits 420 are connected in series between a pair of electrical conductors 1001, 1002 previously described, and testing circuits 420' are connected in series between a pair of electrical conductors 1003, 1004 previously described. Although four sensors 500 are shown in this embodiment, in general, any number of sensors (e.g., sensors 500) may be included in the array (e.g., array 1500). For most applications, array 1500 preferably includes four to eight sensors 500, although more may be desirable.

By applying a voltage differential across conductors 1001, 1002 and measuring the current flow therethrough, the total resistance across all testing circuits 420 is determined. As long as elements 224 in circuits 420 are intact, the determined resistance between wires 1001, 1002 will be very low (~0 ohms). However, if any one or more of testing elements 224 in circuits 420 have corroded through, it will create an open circuit between conductors 1001, 1002 and the determined resistance will be very high. Likewise, by applying a voltage differential across conductors 1003, 1004 and measuring the current flow therethrough, the total resistance across all circuits 420' is determined. As long as elements 224 in circuits 420' are intact, the determined resistance between wires 1003, 1004 will be very low (~0 ohms). However, if any one or more of testing elements 224 in circuits 420' have corroded through, it will create an open circuit between conductors 1003, 1004 and the determined resistance will be very high.

Since each sensor 500 includes an element 224 at each end 110a, b, array 1500 may be installed and operated in the same manner as array 1200 or array 1300 previously described. In other words, array 1500 may be employed to detect corrosion in an original weld pack 20 (i.e., at an interface between insulation 16 and the axially adjacent insulation 13) or in a rehabilitated weld pack 20' (i.e., at an interface between insulation 13 and barrier 18).

Using array 1500, an inspector can interrogate all circuits 420 with one resistance determination, and interrogate all circuits 420' with one resistance determination. The resistance across all circuits 420 provides the inspector with information about whether an element 224 in one or more of circuits 420 has corroded through, and the resistance across all circuits 420' provides the inspector with information about whether an element 224 in one or more circuits 420' has corroded through. However, unlike array 1400 previously described, in this embodiment, by employing resistors 430 with different, known resistances in array 1500, knowing the resistance of each resistor 430 in each sensor 500, and knowing the position of each sensor 500, the particular sensors 500 having corroded elements 224, and hence the CUI susceptible areas on pipe segments 11 at which corrosion has occurred, may be determined in the manner previously described with reference to FIG. 25-27.

In the embodiments of arrays 1000, 1100, 1200, 1300, 1400, 1500 previously described, a plurality of testing circuits in different sensors are coupled together in series. While this simplifies interrogation of the circuits since all circuits connected together in series can be interrogated by the inspector at one time (i.e., with a single resistance determination), it may not enable the inspector to identify which particular testing elements 224 have corroded or the locations of the corrosion, particularly with respect to arrays 1000, 1100, 1200, 1300, 1400. Thus, in some embodiments, the array may include a plurality of distinct and separate individual sensors (e.g., sensors 100, 200, 200', 300, 400, 400', 500, 600, 700) disposed in the weld pack 20, 20' in the same manner as shown and described above with respect to the sensors in arrays 1000, 1100, 1200, 1300, 1400, 1500. Since each individual sensor has its own set of conductors, each sensor may be independently interrogated by the inspector, thereby enabling the inspector to identify each specific sensor that has an element that is corroded through. However, this approach may be time consuming (e.g., to individually check six or eight independent sensors in a single weld pack), and further, enhance the opportunity for ingress of moisture into the weld pack since multiple pairs of testing conductors will be extending from the weld pack. Accordingly, in embodiments of arrays including multiple independent sensors to be separately interrogated, a multiplexer is preferably employed to facilitate the interrogation of multiple independent sensors.

Figure 33:
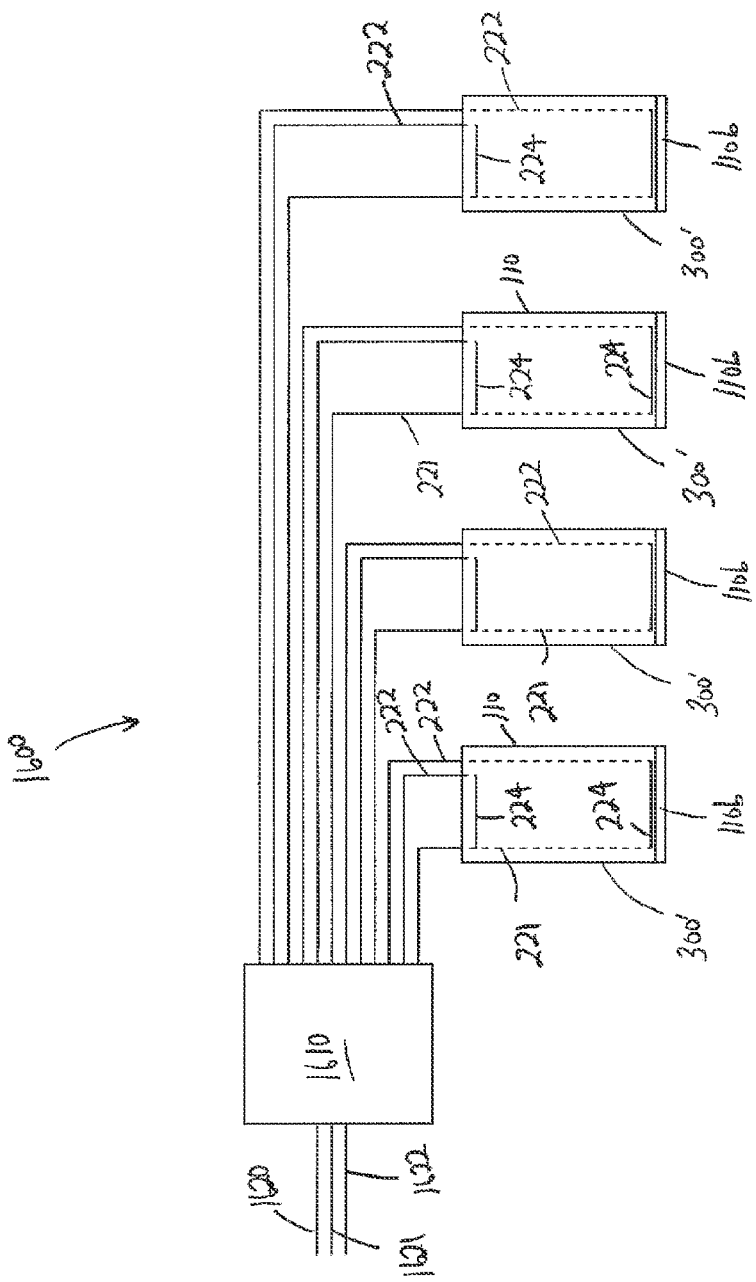
FIG. 33 is a front view of an embodiment of an array of CUI sensors in accordance with the principles described herein.

Referring now to FIG. 33, an embodiment of an array 1600 including a plurality of sensors 300' coupled to a multiplexor 1610 is shown. Each sensor 300' is the same as sensor 300 previously described with the exception that elements 224 in each sensor 300' are coupled to a common conductor 221. Each conductor 221 and each pair of conductors 222 from each sensor are coupled to multiplexor 1610. In addition, a plurality of electrical conductors 1620, 1621, 1622 extend from multiplexor 1610 and are used by the inspector to interrogate sensor 300' via multiplexor 1610. Unlike arrays 1000, 1100, 1200, 1300, 1400, 1500 previously described, in this embodiment, sensors 300' are not connected in series, and further, elements 224 in different sensors 300' are not connected in series. Rather, each element 224 in each sensor 300' is individually interrogated in sequence by multiplexor 1610, thereby allowing the individual identification of the specific sensors 300' having elements 224 that are corroded through.

To monitor and detect corrosion in an original weld pack 20, sensors 300' of array 1600 are preferably installed in the same manner as sensors 200 of array 1000 previously described, and to monitor and detect corrosion in a rehabilitated weld pack 20', sensors 300' of array 1600 are preferably installed in the same manner as sensors 200' of array 1100 previously described. Multiplexor 1610 is preferably disposed within the weld pack 20, 20' (e.g., under jacket 15, 15') to protect multiplexor 16010 and reduce the number of penetrations of jacket 15, 15' and/or seals 17, 17'. In particular, by positioning multiplexor 1610 within the weld pack 20, 20', only conductors 1620, 1621, 1622, as opposed to every conductor 221, 222, needs to penetrate jacket 15, 15' and/or seals 17, 17' for inspection.

Figure 34:
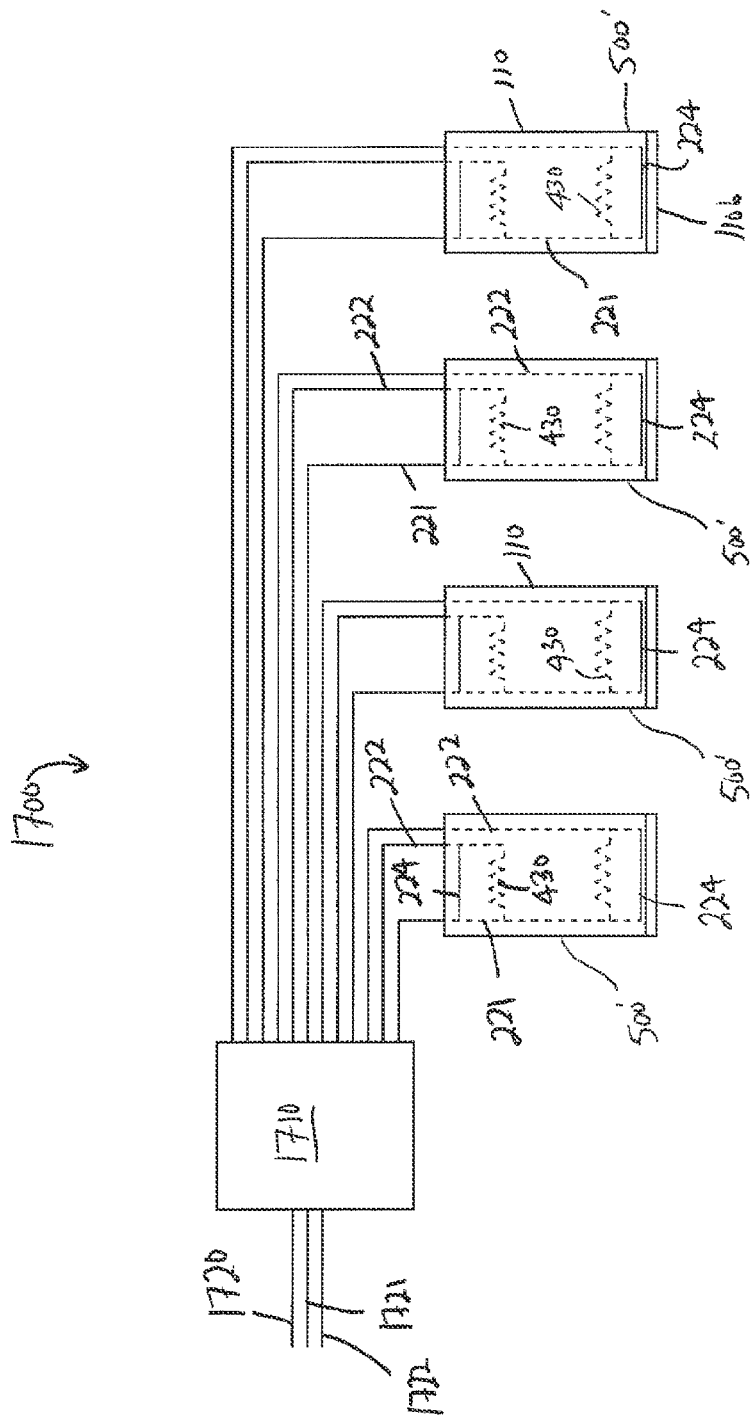
FIG. 34 is a front view of an embodiment of an array of CUI sensors in accordance with the principles described herein.

Referring now to FIG. 34, an embodiment of an array 1700 including a plurality of sensors 500' coupled to a multiplexor 1710 is shown. Each sensor 500' is the same as sensor 500 previously described with the exception that elements 224 and resistors 430 in each sensor 500' are coupled to a common conductor 221. Each conductor 221 and each pair of conductors 222 from each sensor are coupled to multiplexor 1710. In addition, a plurality of electrical conductors 1720, 1721, 1722 extend from multiplexor 1710 and are used by the inspector to interrogate sensor 500' via multiplexor 1710. Unlike arrays 1000, 1100, 1200, 1300, 1400, 1500 previously described, in this embodiment, sensors 500' are not connected in series, and further, elements 224 in different sensors 500' are not connected in series. Rather, each element 224 in each sensor 500' is individually interrogated in sequence by multiplexor 1710, thereby allowing the individual identification of the specific sensors 500' having elements 224 that are corroded through.

To monitor and detect corrosion in an original weld pack 20, sensors 500' of array 1700 are preferably installed in the same manner as sensors 200 of array 1000 previously described, and to monitor and detect corrosion in a rehabilitated weld pack 20', sensors 500' of array 1700 are preferably installed in the same manner as sensors 200' of array 1100 previously described. Multiplexor 1710 is preferably disposed within the weld pack 20, 20' (e.g., under jacket 15, 15') to protect multiplexor 17010 and reduce the number of penetrations of jacket 15, 15' and/or seals 17, 17'. In particular, by positioning multiplexor 1710 within the weld pack 20, 20', only conductors 1720, 1721, 1722, as opposed to every conductor 221, 222, needs to penetrate jacket 15, 15' and/or seals 17, 17' for inspection.

Figure 35:
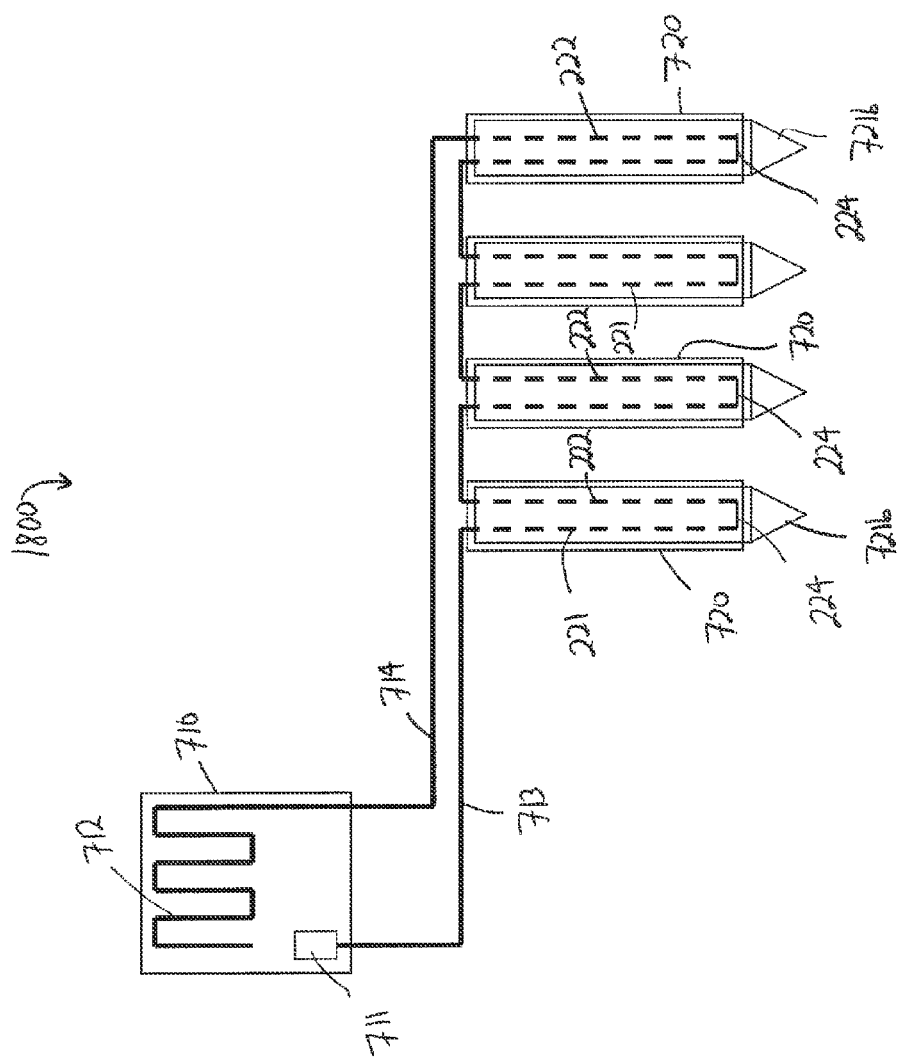
FIG. 35 is a front view of an embodiment of the CUI sensor of FIG. 15 including a plurality of testing members.

Referring now to FIG. 35, an embodiment of an array 1800 including RFID tag 710 previously described and a plurality of CUI testing members 720 previously described is shown. Circuit 711 is coupled to antenna 712 through testing members 720. In other words, circuit 711 and antenna 712 communicate with each other through testing members 720. Testing members 720 are connected in series between wires 713, 714 previously described. Although this embodiment of array 1800 includes testing members 720 with elements 224 positioned adjacent end 721b, in other embodiments, testing members 720 may include elements 224 positioned adjacent end 721a as shown in FIG. 16.

To monitor and detect corrosion in an original weld pack 20, testing members 720 of array 1800 are preferably installed in the same manner as sensors 200 of array 1000 previously described. To monitor and detect corrosion in a rehabilitated weld pack 20', elements 224 are preferably positioned adjacent end 721a as shown in FIG. 16, and testing members 720 are preferably installed in the same manner as sensors 200' of array 1100 previously described.

To assess whether any element 224 has corroded, indicating pipe segment 11 may have corroded, the reader is pass over or aimed at RFID tag 710. If each element 224 is intact, RFID tag 710 will respond to the reader, however, if any one element 224 is corroded through, then circuit 711 cannot communicate with antenna 712 and RFID tag 710 will not respond to the reader. Therefore, by simply passing the reader across RFID tag 710, inspectors can easily assess whether any element 224 is corroded, thereby enhancing the speed and ease with which corrosion may be identified.

As previously described, RFID tag 710 is preferably external weld pack 20, 20' in embodiments where jacket 15, 15', respectively, is metal. Consequently, its location may be visually identified for interrogation. However, a second, conventional RFID tag 750 is preferably positioned immediately adjacent RFID tag 710 to allow automatic recording of corrosion data and location regardless of the state of RFID tag 710 as previously described.

Embodiments of sensors and arrays herein are shown and described as being installed on pipelines that utilize foam-in-place insulation (i.e., shop-applied foam insulation 16 injected in the annulus between jacket 15 and pipe segments 11). However, in general, embodiments of sensors and arrays described herein may be installed along any insulated pipeline, pipe joint, or pipe segment to monitor and detect CUI. For example, some pipelines utilize "preformed" insulation to insulate pipe segments. More specifically, the pipeline are fabricated in the field using uninsulated steel pipe sections. After the pipe sections are connected together end-to-end to form the pipeline, they are insulated by applying sections of preformed insulation such as half-shells of polyurethane foam, which is then wrapped in a protective jacket similar to jacket 15. The primary differences between preformed insulation and foam-in-place insulation are that (a) preformed insulation is not bonded to the underlying pipe segment, and (b) when water penetrates the jacketing around the preformed insulation, it can migrate around the preformed insulation and reach the outer surface of the underlying pipe segment. Due to these differences, it is generally not appropriate to insert CUI sensors into preformed insulation. Rather, for preformed insulation, the sensor(s) are preferably positioned on the outer surface of the pipe segment radially between the pipe segment and the preformed insulation. Since preformed insulation is easily removed, the sensor(s) can easily be positioned in this manner during initial installation of the preformed insulation or during a retrofit.

Figure 36:
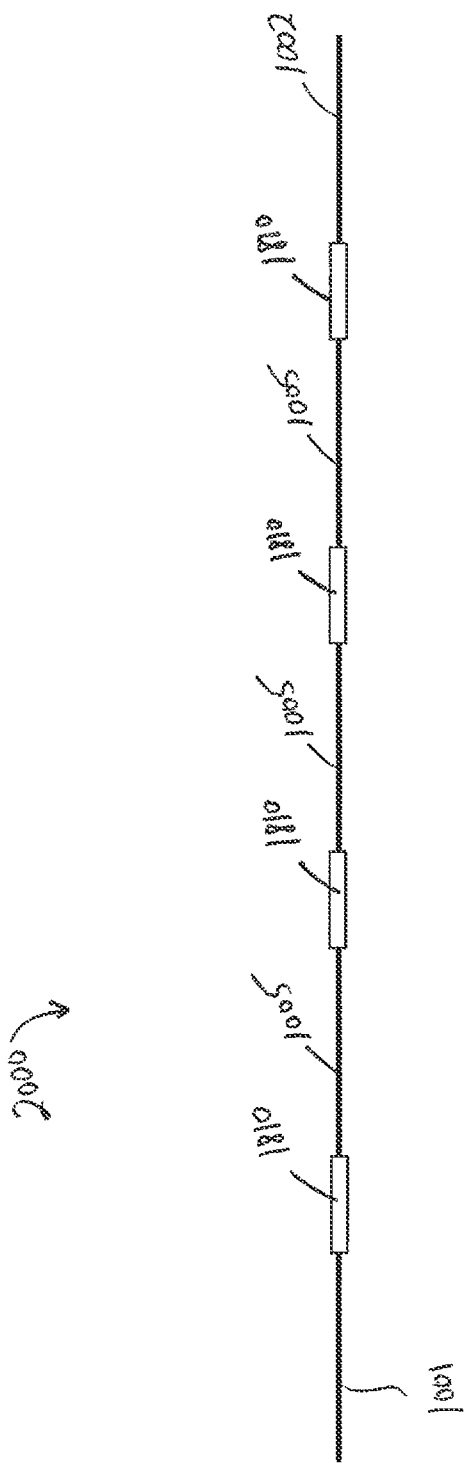
FIG. 36 is a front view of an embodiment of an array of CUI sensors in accordance with the principles described herein.
Figure 37:
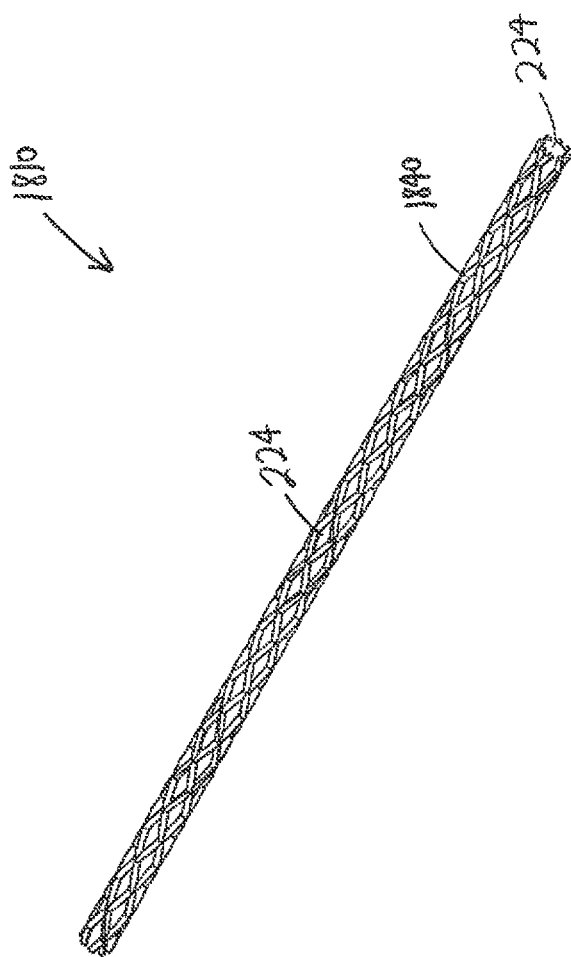
FIG. 37 is a perspective view of one of the CUI sensors of the array of FIG. 36.

Referring now to FIG. 36, an embodiment of an array 2000 of CUI sensors 1810 particularly suited for detecting CUI in preformed insulation and rehabilitated weld packs 20' is shown. In this embodiment, array 2000 is an elongate strand including a plurality of sensors 1810 connected in series between a pair of electrical conductors 1001, 1002. One conductor 1005 extends between each pair of adjacent sensors 1810. In this embodiment, conductors 1001, 1002, 1005 are insulated wires. As best shown in FIG. 37, each sensor 1810 includes an element 224 as previously described disposed within a porous insulator 1840. Each end of each element 224 is electrically coupled to one conductor 1001, 1002, 1005. When element 224 is positioned radially adjacent a pipe segment 11, insulator 1840 prevents element 224 from directly contacting the pipe segment 11, while allowing element 224 to be exposed to the same environment (e.g., temperature and moisture) as the pipe segment 11. In this embodiment, insulator 1840 is a mesh made of a non-metal such as plastic Although four sensors 1810 are shown in this embodiment, in general, any number of sensors (e.g., sensors 1810) may be included in the array (e.g., array 2000). For most applications, array 2000 preferably includes four to eight sensors 1810, although more may be desirable.

By applying a voltage differential across conductors 1001, 1002 and measuring the current flow through array 2000, the total resistance across all testing elements 224 is determined. As long as each element 224 is intact, the determined resistance between wires 1001, 1002 will be very low (~0 ohms). However, if any one or more of testing elements 224 have corroded through, it will create an open circuit between conductors 1001, 1002 and the determined resistance will be very high.

Figure 38:
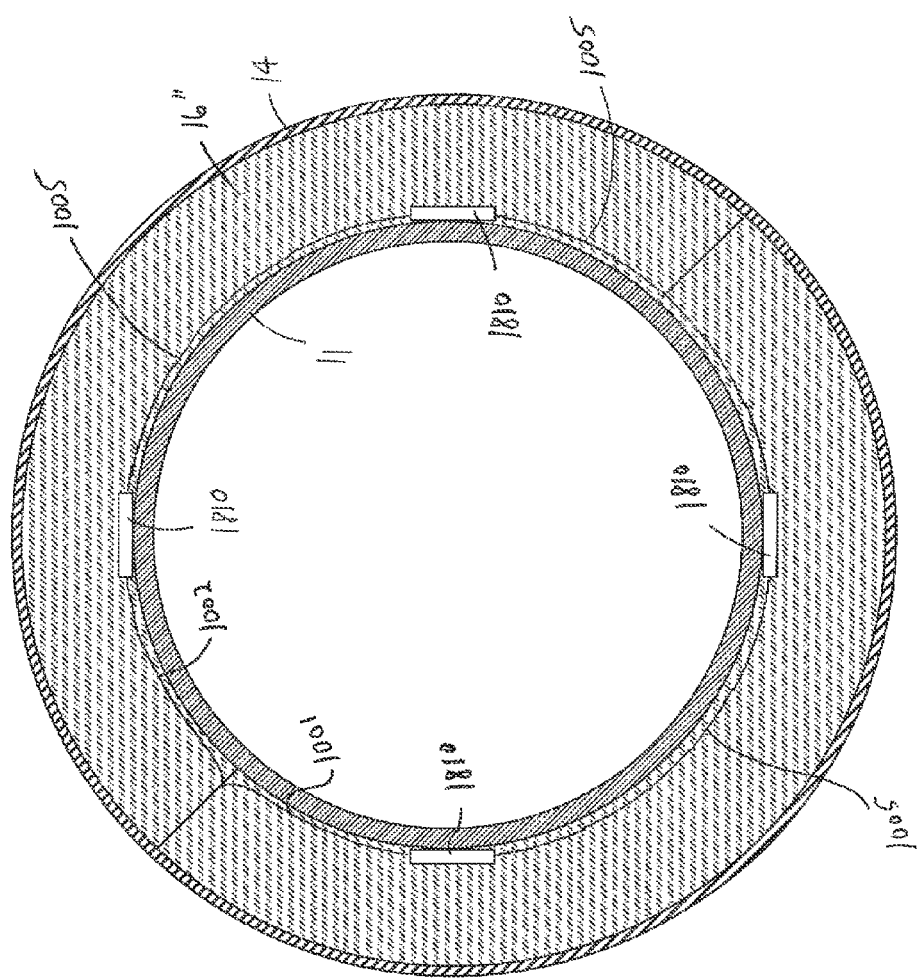
FIG. 38 is a cross-sectional end view of the array of FIG. 36 installed on an insulated pipe segment.

Referring now to FIGS. 36 and 38, one or more arrays 2000 are wrapped around the portion of a pipe segment 11 to be monitored for CUI. Since the array 2000 is wrapped around the pipe segment 11, it is most suited for application when no insulation is disposed about the pipe segment 11. For example, array 2000 may be wrapped around pipe segment 11 before preformed insulation is disposed about the pipe segment 11, or wrapped around the pipe segment 11 following removal of insulation 16 and before application of barrier 18 and insulation 16' in a rehabilitated weld pack 20'. In FIG. 37, one exemplary array 2000 is shown installed on a pipe segment 11 insulated with preformed insulation 16". For a rehabilitated weld pack 20', array 2000 is preferably disposed between the pipe segment 11 and insulation 13 axially adjacent the interface of insulation 13 and barrier 18. Conductors 1001, 1002 of array 2000 are routed through insulation 16', 16", a seal 17', or through jacket 15' to the environment outside weld pack 20 so that they can be easily accessed.

As discussed above, the lower portion of a pipe segment 11 is typically the area of the pipe segment 11 most likely to get wet and start corroding first. Accordingly, at least one sensor 1810 is preferably positioned along the lower half of the pipe segment 11. In this embodiment, sensors 1810 of array 2000 are uniformly circumferentially-spaced 90° apart with one sensor 1810 disposed at bottom dead center of its corresponding pipe segment 11 (the 6 o'clock position) as this is a high-probability of corrosion location. In other words, sensors 1810 of each array 1000 may be described as being disposed at the 3, 6, 9, and 12 o'clock positions.

Although sensors 1810 of array 2000 are described as being uniformly circumferentially-spaced about the entire circumference of an associated pipe segment 11, in other embodiments, sensors 1810 of an array 2000 may be non-uniformly circumferentially-spaced, concentrated in a particular portion of the circumference of the associated pipe segment 11, or combinations thereof.

Referring still to FIGS. 36 and 38, to inspect each pipe segment 11, a meter is employed to apply a voltage differential across conductors 1001, 1002 of the array 2000, measure the current in conductors 1001, 1002, and determine the total resistance across all testing elements 224 in array 2000. If each element 224 is intact, the measured resistance between wires 1001, 1002 will be very low (~0 ohms), thereby indicating very little, if any, corrosion of the CUI susceptible areas of pipe segments 11 within weld pack 20. However, if any one or more of testing elements 224 have corroded through, the measured resistance between wires 1001, 1002 will be relatively high, thereby indicating corrosion of at least one CUI susceptible area of pipe segments 11. Since element 224 in each array 2000 are in series and a relatively high resistance will occur if any one or more elements 224 corrodes completely through, a relatively high resistance is only indicative of corrosion somewhere proximate one or more element 224. Thus, although this embodiment enables a relatively quick, non-invasive identification of whether corrosion is or is not occurring, it does not enable the inspector to determine which specific element 224 corroded through, the specific location of the corrosion, how many elements 224 corroded through, or whether the corrosion is occurring at multiple locations. Consequently, if no corrosion is detected with array 2000, the inspectors can promptly move on and inspect another array 2000, weld pack or CUI susceptible area of the pipeline. However, if corrosion is detected with an array 2000, a subsequent inspection such as a TRT inspection is preferably performed to better locate, examine, and assess the corrosion.

Figure 39:
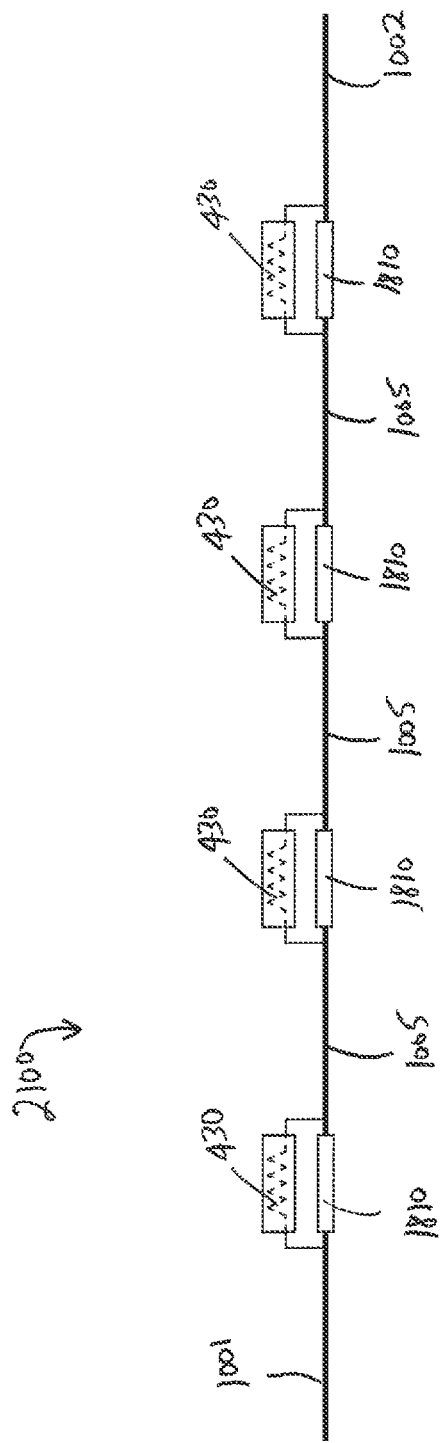
FIG. 39 is a front view of an embodiment of an array of CUI sensors in accordance with the principles described herein.

Referring now to FIG. 39, an embodiment of an array 2100 of sensors 1810 as previously described and particularly suited for detecting CUI in preformed insulation and rehabilitated weld packs 20' is shown. Array 2100 is the same as array 2000 previously described with the exception that a reference resistor 430 as previously described is placed in parallel with each sensor 1810. Each resistor 430 is embedded or coated in a non-conductive insulating material such as epoxy, plastic or fiberglass laminate to prevent resistor 430 from corroding.

By applying a voltage differential across conductors 1001, 1002 and measuring the current flow through array 2100, the total resistance between conductors 1001, 1002 is determined. As long as each element 224 is intact, the determined resistance between wires 1001, 1002 will be very low (~0 ohms). However, if any testing element 224 has corroded through, the resistance of its corresponding resistor 430 will be included in the determined resistance between wires 1001, 1002. For example, assuming each resistor 430 has a resistance of 10 ohms, if one element 224 corrodes through, the determined resistance will be about 10 ohms; if two elements 224 corrode through, the determined resistance will be about 20 ohms; if three elements 224 corrode through, the determined resistance will be about 30 ohms, and so on.

One or more arrays 2100 may be installed in the same manner as array 2000 previously described. As a result, elements 224 is positioned radially proximate pipe segment 11. Once installed, array 2100 is operated in the same manner as array 2000 to detect corrosion in pipe segment 11. In particular, to inspect pipe segments 11, a meter is employed to apply a voltage differential across conductors 1001, 1002 of array 2100, measure the current in conductors 1001, 1002, and determine the total resistance between conductors 1001, 1002. If each element 224 is intact, the measured resistance between wires 1001, 1002 will be very low (~0 ohms), thereby indicating very little, if any, corrosion of the CUI susceptible areas of pipe segment 11. However, if any one or more of testing elements 224 have corroded through, the measured resistance between wires 1001, 1002 will be about the same as the sum of the resistances of the resistors 430 associated with each element 224 that has corroded through, thereby indicating corrosion of one or more CUI susceptible areas of pipe segments 11. If each resistor 430 has a known resistance, the number of elements 224 that have corroded can be calculated. For example, if each resistor 430 in an array 1200 has a resistance of 10 ohms and the resistance across all sensors 224 in that array 1200 is ~40 ohms, then all four elements 224 have corroded through, thereby indicating that four CUI susceptible areas of pipe segments 11 have corroded.

By employing resistors 430 with different, known resistances in array 2100, knowing the resistance of resistor 430, and knowing the position of each element 224, the particular elements 224 that have corroded through, and hence the CUI susceptible areas on pipe segments 11 at which corrosion has occurred, may be determined in the manner previously described with respect to array 1200. To ensure the corrosion of different sets of two or more elements 224 in array 2100 cannot yield the same total determined resistance, the resistances of the resistors 430 in array 2100 may be arranged such that each subsequent resistor 430 in the array 2100 has twice the resistance of the previous resistor 430 in the array 2100.

If no corrosion is detected with an array 2100, the inspectors can promptly move on and inspect another array 2100, weld pack or CUI susceptible area of the pipeline. However, if corrosion is detected with an array 2100, a subsequent inspection of the corroded area such as a TRT inspection is preferably performed to better locate, examine, and assess the corrosion.

In the manners described, embodiments of sensors and arrays disclosed herein may be installed on insulated pipelines to monitor and detect CUI. To inspect the pipeline, an inspection crew moves down the pipeline until they came upon a CUI susceptible location having sensor(s) installed (e.g., at a weld pack). Next, the crew interrogates the sensor(s) to identify any potential CUI. If no potential corrosion is detected, the crew records the result and moves to the next CUI susceptible location with sensor(s) installed. However, if there is an indication that CUI is present, the crew more thoroughly inspects the location using TRT or other suitable CUI inspection technique. This approach offers the potential to eliminate up to 96% of TRT inspections (if all CUI-susceptible locations were instrumented with CUI sensors).

For existing pipelines, embodiments of CUI sensors would likely be installed only at weld packs being rehabilitated and at weld packs where previous TRT inspections indicated significant amount of moisture in the insulation. In the latter case, these weld packs are candidates for installation of "preventive barriers" such as water-proof barrier 18. In either case (rehabilitating a weld pack or installing a preventive barrier), the existing field-applied metal jacketing 15 is removed in the process and is later replaced with new jacketing 15'. Removal of the metal jacketing 15 greatly facilitates installation of CUI sensors at a weld pack 20, 20', and since the jacketing 15 is replaced anyway, installation of CUI sensors can be done for virtually just the incremental cost of the CUI sensors themselves.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simply subsequent reference to such steps.

What is claimed is:

1. A method of sensing corrosion of a pipe covered by a layer of insulation, the method comprising:
   inserting a CUI sensor radially through the layer of insulation to a location adjacent an outer surface of the pipe, wherein the CUI sensor comprises:
      a non-conductive base having a first end and a second end opposite the first end, wherein the inserting step positions the first end of the base distal the pipe and the second end of the base adjacent the pipe; and
      at least one test circuit mounted to the base, wherein each test circuit includes a first conductor, a second conductor, and a testing element extending between the first conductor and the second conductor;
   exposing the testing element to the same environment as the outer surface of the pipe; and
   determining whether the testing element has corroded through.

2. The method of claim 1, wherein the pipe is made from a metal or metal alloy, and wherein the testing element is made from the same metal or metal alloy as the pipe.

3. The method of claim 1, wherein the testing element is a wire filament having a diameter between 5 mil and 20 mil.

4. The method of claim 3, wherein the determining step comprises evaluating a resistance across the testing element.

5. The method of claim 3, wherein the CUI sensor includes an RFID tag including an antenna and an integrated RFID circuit,
   wherein the first conductor is coupled to the RFID circuit and the second conductor is coupled to the antenna;
   wherein the determining step comprises determining whether the RFID circuit can communicate via the antenna.

6. The method of claim 1, wherein the testing element is positioned adjacent the second end of the base.

7. The method of claim 1, wherein the inserting step inserts each of a first plurality of CUI sensors radially through the layer of insulation to a location adjacent an outer surface of the pipe,
   wherein each CUI sensor in the first array comprises:
      a non-conductive base having a first end and a second end opposite the first end, wherein the inserting step positions the first end of the base distal the pipe and the second end of the base adjacent the pipe; and
      at least one test circuit mounted to the base, wherein each test circuit includes a first conductor, a second conductor, and a testing element extending between the first conductor and the second conductor;
   wherein the exposing step comprises exposing the testing element of each of the first plurality of CUI sensors to the same environment as the outer surface of the pipe; and
   determining whether the testing element of any of the first plurality of CUI sensors has corroded through.

8. The method of claim 7, wherein the testing element of each CUI sensor is a wire filament having a diameter between 5 mil and 20 mil.

9. The method of claim 7, wherein the inserting step comprises inserting the first plurality of sensors circumferentially about the pipe.

10. The method of claim 9, wherein the inserting step inserts at least one of the first plurality of CUI sensors at the bottom dead center of the pipe.

11. The method of claim 9, wherein the inserting step inserts the plurality of CUI sensors in the first array at a uniform circumferential spacing about the pipe.

12. The method of claim 9, further comprising:
   inserting each of a second plurality of CUI sensors radially through the layer of insulation to a location adjacent an outer surface of the pipe, circumferentially about the pipe relative to one another, and at a location axially spaced from the first plurality of CUI sensors,
   wherein each CUI sensor in the second array comprises:
      a non-conductive base having a first end and a second end opposite the first end;
      at least one test circuit mounted to the base, wherein each test circuit includes a first conductor, a second conductor, and a testing element extending between the first conductor and the second conductor;
   exposing the testing element of each CUI sensor in the second plurality of CUI sensors to the same environment as the outer surface of the pipe; and
   determining whether the testing element of each CUI sensor in the second plurality of CUI sensors has corroded through.

13. The method of claim 9, wherein the inserting step inserts a first of the plurality of the CUI sensors at the bottom dead center of the pipe, inserts a second of the plurality of the CUI sensors circumferentially spaced less than or equal to 90° in a clockwise direction from the first of the plurality of CUI sensors, and inserts a third of the plurality of CUI sensors circumferentially spaced less than or equal to 90° in a counterclockwise direction from the first of the plurality of the CUI sensors.

14. The method of claim 7, further comprising connecting the test circuits of the CUI sensors in the first plurality of CUI sensors in series.

15. The method of claim 1, wherein the test circuit of the CUI sensor further comprises a reference resistor extending between the first conductor and the second conductor; wherein the reference resistor is in parallel with the testing element.

* * * * *